(12) United States Patent
Spears

(10) Patent No.: US 10,173,030 B2
(45) Date of Patent: Jan. 8, 2019

(54) CATHETER FOR INFUSION OF A CARDIOVASCULAR FLUID

(71) Applicant: Oakwood Healthcare, Inc., Dearborn, MI (US)

(72) Inventor: James R. Spears, Bloomfield Hills, MI (US)

(73) Assignee: Oakwood Healthcare, Inc., Dearborn, MI (US)

( * ) Notice: Subject to any disclaimer, the term of this patent is extended or adjusted under 35 U.S.C. 154(b) by 700 days.

(21) Appl. No.: 14/540,994

(22) Filed: Nov. 13, 2014

(65) Prior Publication Data

US 2015/0141905 A1 May 21, 2015

Related U.S. Application Data

(60) Provisional application No. 61/905,150, filed on Nov. 15, 2013.

(51) Int. Cl.
| | |
|---|---|
| *A61M 37/00* | (2006.01) |
| *A61M 25/00* | (2006.01) |
| *A61M 5/14* | (2006.01) |
| *A61M 5/142* | (2006.01) |
| *A61M 5/172* | (2006.01) |
| *A61M 5/48* | (2006.01) |

(Continued)

(52) U.S. Cl.
CPC ........ *A61M 25/0023* (2013.01); *A61M 5/142* (2013.01); *A61M 5/1407* (2013.01); *A61M 5/172* (2013.01); *A61M 5/482* (2013.01); *A61M 5/484* (2013.01); *A61M 25/003* (2013.01); *A61M 25/0041* (2013.01); *A61M 25/007* (2013.01); *A61M 39/10* (2013.01); *A61M 2005/006* (2013.01); *A61M 2205/3337* (2013.01); *A61M 2205/502* (2013.01); *A61M 2210/12* (2013.01); *A61M 2210/125* (2013.01); *A61M 2210/127* (2013.01)

(58) Field of Classification Search
CPC .. A61M 25/0023; A61M 5/142; A61M 5/482; A61M 5/484; A61M 25/003
USPC ......................................................... 604/24
See application file for complete search history.

(56) References Cited

U.S. PATENT DOCUMENTS

| | | | | |
|---|---|---|---|---|
| 4,072,146 A | * | 2/1978 | Howes | ............... A61B 5/02152 600/487 |
| 4,153,048 A | * | 5/1979 | Magrini | ................. A61B 5/028 600/505 |
| 4,318,402 A | | 3/1982 | Vaillancourt | |

(Continued)

*Primary Examiner* — Edelmira Bosques
(74) *Attorney, Agent, or Firm* — Dykema Gossett PLLC

(57) ABSTRACT

Catheters for infusion of cardiovascular fluids into blood are disclosed. The cardiovascular fluid may, for example, comprise water highly supersaturated with a gas such as oxygen. Each catheter comprises one or more capillary tubings (or capillaries) through which a cardiovascular fluid flows. The distal end of each capillary is mounted (e.g., potted) preferably flush with an external surface of a catheter sidewall, while the proximal end of each capillary is in fluid communication with a cardiovascular fluid flowing through the lumen of the catheter. The combination of the catheter shape and the orientation of the distal end of each capillary relative to the longitudinal axis of the catheter provides control over the mixing pattern of the cardiovascular fluid with blood flowing within a vascular space such as an aorta.

38 Claims, 17 Drawing Sheets

(51) Int. Cl.
   *A61M 39/10*      (2006.01)
   *A61M 5/00*       (2006.01)

(56) References Cited

U.S. PATENT DOCUMENTS

| | | | | |
|---|---|---|---|---|
| 4,817,624 | A * | 4/1989 | Newbower | A61B 5/028 |
| | | | | 600/505 |
| 5,086,620 | A | 2/1992 | Spears | |
| 5,145,567 | A * | 9/1992 | Hsieh | C12Q 1/007 |
| | | | | 204/452 |
| 5,304,171 | A * | 4/1994 | Gregory | A61B 18/245 |
| | | | | 385/125 |
| 5,407,426 | A | 4/1995 | Spears | |
| 5,569,180 | A | 10/1996 | Spears | |
| 5,599,296 | A | 2/1997 | Spears | |
| 5,797,874 | A | 8/1998 | Spears | |
| 5,833,659 | A | 11/1998 | Kranys | |
| 6,180,059 | B1 | 1/2001 | Divino et al. | |
| 6,248,087 | B1 | 6/2001 | Spears et al. | |
| 6,454,997 | B1 | 9/2002 | Divino et al. | |
| 6,607,698 | B1 | 8/2003 | Spears et al. | |
| 2001/0016764 | A1 * | 8/2001 | Dobak, III | A61F 7/12 |
| | | | | 607/105 |
| 2002/0025576 | A1 * | 2/2002 | Northrup | G01N 27/44743 |
| | | | | 435/288.5 |
| 2006/0074398 | A1 * | 4/2006 | Whiting | A61M 25/0041 |
| | | | | 604/510 |
| 2008/0119693 | A1 * | 5/2008 | Makower | A61B 1/00135 |
| | | | | 600/114 |
| 2008/0200877 | A1 | 8/2008 | Panotopoulos | |
| 2012/0053565 | A1 | 3/2012 | Lee | |

\* cited by examiner

CATHETER FOR INFUSION OF A CARDIOVASCULAR FLUID

CROSS REFERENCE TO RELATED APPLICATIONS

This application claims the benefit of U.S. provisional application No. 61/905,150, filed 15 Nov. 2013, which is hereby incorporated by reference as though fully set forth herein.

BACKGROUND a. Field

The instant disclosure relates to catheters for infusing cardiovascular fluids or solutions into blood vessels. The infused fluids may be used for oxygen therapy to treat various tissue conditions and other ailments.

b. Background Art

Catheters are used in a variety of diagnostic and therapeutic procedures, including oxygen therapy procedures. For example, it has been found that delivering oxygen supersaturated fluid to damaged tissue (e.g., infarcted tissue after a heart attack) can help mitigate the damage and potentially facilitate tissue recovery (e.g., reducing infarct size). It is thought that infusing an oxygen supersaturated fluid (for example, saline supersaturated with oxygen or "aqueous oxygen" (AO)) onto tissue greatly facilitates diffusion of the oxygen into that tissue (e.g., diffusing oxygen into ischemic tissue).

A disadvantage of one existing system for infusing oxygen onto tissue is the need for an extracorporeal blood circuit for mixing a cardiovascular fluid (e.g., oxygen supersaturated saline) with the patient's blood to create super-oxygenated blood. In this system, AO is infused into blood flowing in a small extracorporeal circuit. The current application is the infusion of blood that is supersaturated with AO into a coronary artery after stenting for an acute myocardial infarction. The geometry of mixing AO with blood is well controlled, along with the equilibrium $O_2$ concentration achieved in blood resulting from AO infusion. There are several important limitations with this approach. Withdrawing blood such as with a roller pump requires a separate withdrawal line, and the level of negative pressure in the line must be carefully monitored to prevent inadvertent cavitation. Platelet activation and plastic tube spallation by the roller pump are potential concerns, as is the potential thrombogenicity of the extracorporeal circuit. Finally, the extracorporeal circuit is not scalable easily to treat systemic problems, such as hemorrhagic shock and respiratory insufficiency. Very large tubings and catheters, similar to ones used for membrane oxygenators, would be required to supplement systemic oxygen needs.

The foregoing discussion is intended only to illustrate the present field and should not be taken as a disavowal of claim scope.

BRIEF SUMMARY

It is desirable to be able to infuse highly gas supersaturated aqueous solutions into host liquids without bubble nucleation despite thermodynamic instability. This is possible under well-defined conditions even though complete elimination of surface nuclei is not usually realistic.

It is also desirable to eliminate the need for an extracorporeal circuit by directly infusing AO into the aorta or other major vascular spaces without significant bubble formation. Additionally, it is desirable to provide sufficient oxygen to enhance systemic oxygenation. The latter effect finds utility not only for treatment of systemic problems such as respiratory insufficiency and shock states (e.g., cardiogenic, septic, hemorrhagic, neurogenic, anaphylactic), but also for regional tissue problems such as myocardial infarction and stroke. The relative simplicity of placement of an intra-aortic catheter, which could be accomplished quickly without fluoroscopy, compared to the current practice of delivering blood supersaturated with AO subselectively into a small coronary artery (requiring special catheters, guidewires, and fluoroscopy), would be advantageous In one embodiment, a fluid-delivery catheter comprising (a) a first tubing having a relatively large lumen extending from a proximal end to a distal portion for receiving a cardiovascular fluid; and (2) a second tubing or plurality of second tubings having dimensions substantially smaller than the first tubing and a relatively small lumen that extends from a proximal end to a distal end, with the proximal end of the second tubing(s) positioned within the lumen of the first tubing and providing fluid communication therethrough to the distal end of the second tubing(s), with the distal end of the second tubing(s) positioned through the wall of the first tubing in a distal portion of the first tubing.

The foregoing and other aspects, features, details, utilities, and advantages of the present invention will be apparent by reading the following description and claims, and from reviewing the accompanying drawings.

DETAILED DESCRIPTION OF EMBODIMENTS OF THE INVENTION

A fluid (e.g., water) highly supersaturated with a gas (e.g., oxygen) can be infused into a host liquid (e.g., blood) in a bubbleless manner if heterogeneous nuclei are removed and flow is laminar. A practical method for greatly reducing the number of such nuclei at the solid/liquid interface is to utilize delivery tubings having a luminal surface free of crevices. Rapid growth of submicroscopic pockets of gas, such as air, within crevices, with associated rapid repetitive detachment of the growing bubble, can produce undesirable trains of bubbles at prodigious rates in gas supersaturated solutions. The catheter embodiments depicted in FIGS. 1-12 are designed and configured for infusing cardiovascular fluids (or solutions) into blood vessels while mitigating against the development of undesirable bubbles. While various embodiments are most specifically described herein in the context of infusing fluid onto cardiovascular tissue, it should be recognized that the disclosed catheters are capable of infusing fluids onto various other tissues.

Figure 1:
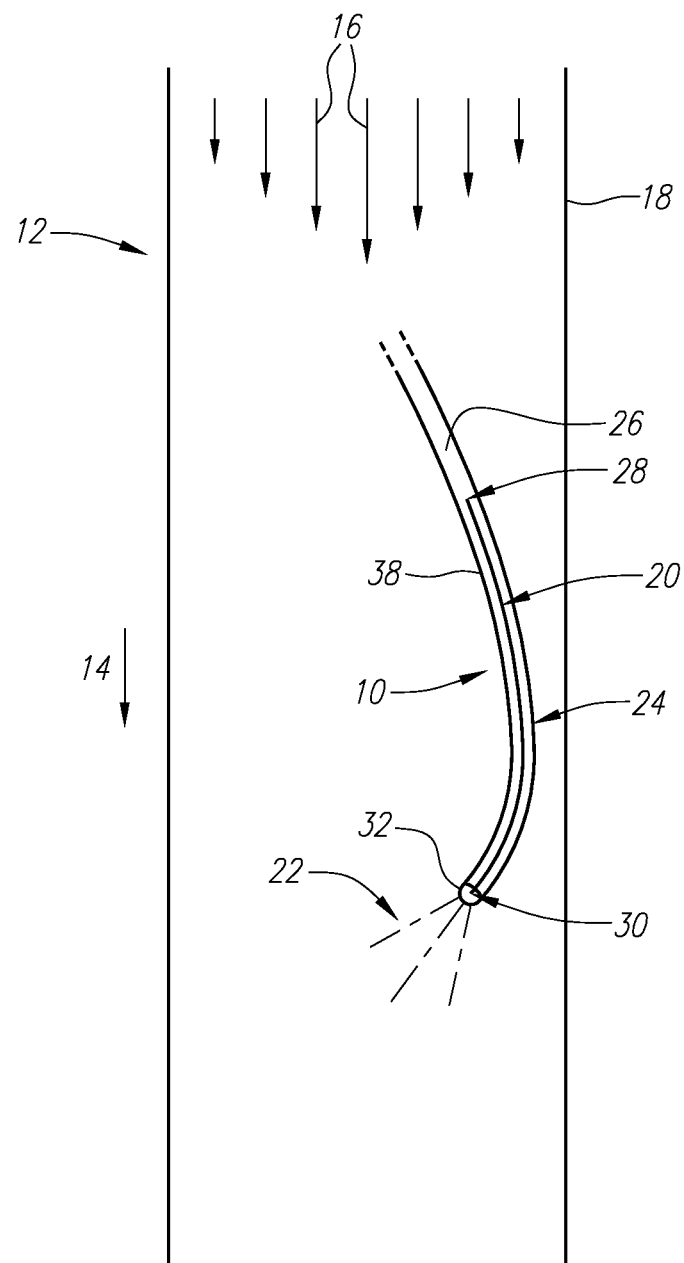
FIG. 1 schematically depicts a distal portion of a first catheter embodiment being advanced antegrade and AO being delivered antegrade.
Figure 2:
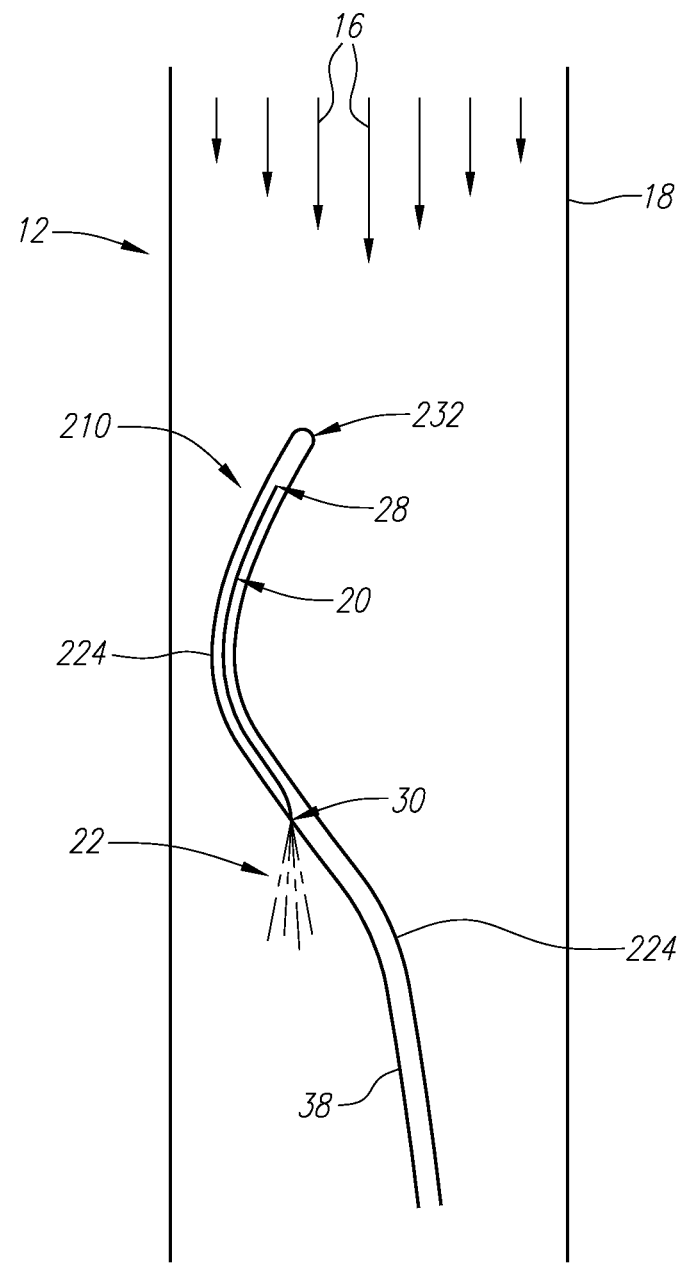
FIG. 2 depicts a distal portion of a second catheter embodiment being advanced retrograde and AO being delivered antegrade.
Figure 3:
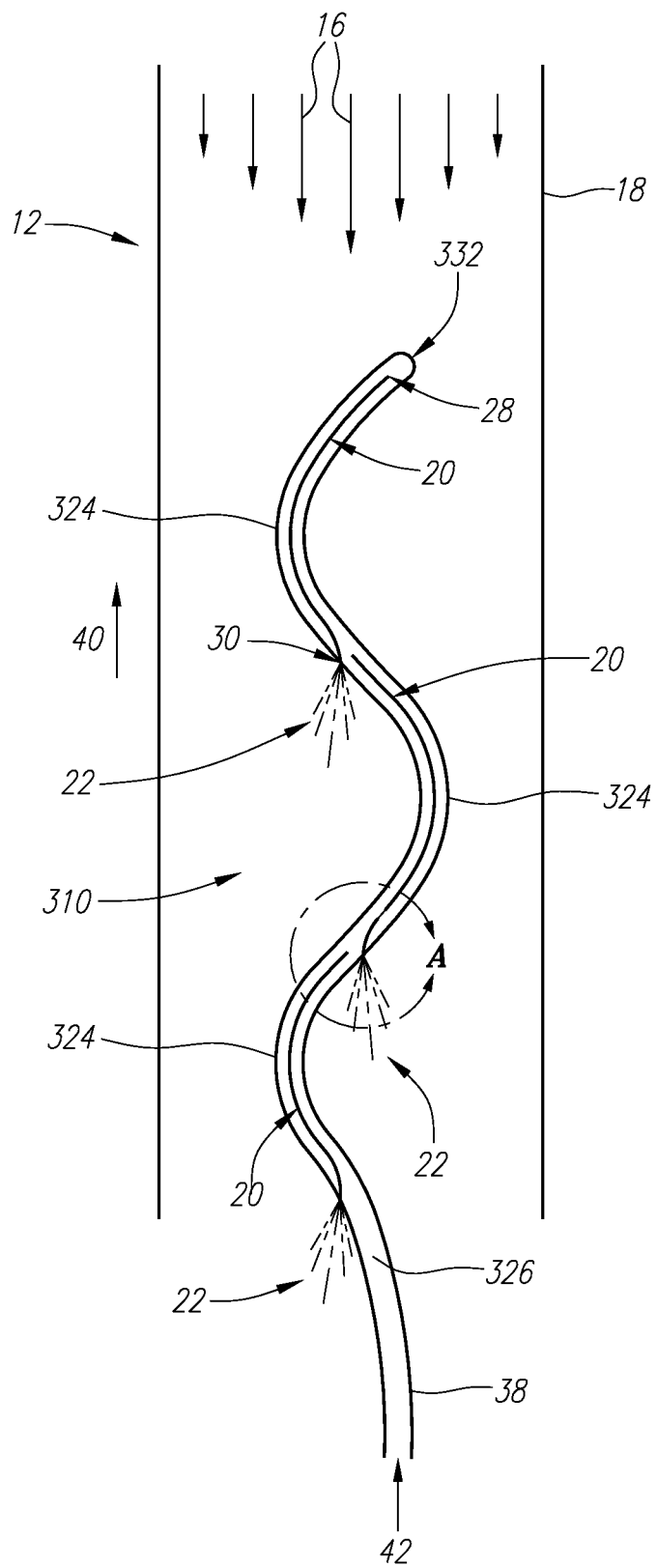
FIG. 3 depicts a distal portion of a sinusoidal catheter having a closed distal end, the catheter being advanced retrograde and delivering AO antegrade from three capillaries toward the center of the artery and away from the artery walls.

FIGS. 1-3 depict substantially two-dimensional representations of infusion catheters according to three different embodiments. FIG. 1 schematically depicts a first catheter 10 being advanced antegrade (e.g., from a radial artery as discussed further below) in an aorta 12 as indicated by arrow 14. The aorta is schematically represented as being perfectly cylindrical. The blood flow through the aorta is represented by the downwardly pointing arrows or indicators 16. The length of these blood flow arrows 16 corresponds to the rate of the blood flow, which is slowest at the walls 18 of the aorta 12 and reaches its maximum in the longitudinal center of the aorta, as represented by the longest downward pointing arrow in FIG. 1. This catheter 10 compromises a capillary tubing (or "capillary") 20 for delivering aqueous oxygen (AO) 22 to tissue (e.g., heart or other organ tissue). This catheter 10 includes a bend 24 designed to ensure that the AO is delivered toward the center of the vessel 12 (e.g., the aorta) and to avoid delivering the AO such that it would immediately impinge upon the wall of the vessel.

As noted, the catheter in this embodiment is being advanced antegrade, as represented by the downward pointing arrow 14. The capillary 20 is mounted inside the catheter lumen 26, and has its proximal end 28 'floating' in the catheter lumen 26 and its distal end 30 mounted adjacent to the distal end 32 of the catheter 10. In particular, the distal end 30 of the capillary may be potted into the end 32 of the catheter 10, so that the distal end of the catheter is closed except for the aqueous oxygen 22 flowing out of the capillary 20. In an alternative to the catheter 10 depicted in FIG. 1 a catheter 10' (see FIG. 1A) may comprise a group of capillaries that are potted with, for example, an epoxy 36 at the distal end 32' of the catheter 10' rather than a single capillary.

Figure 1A:
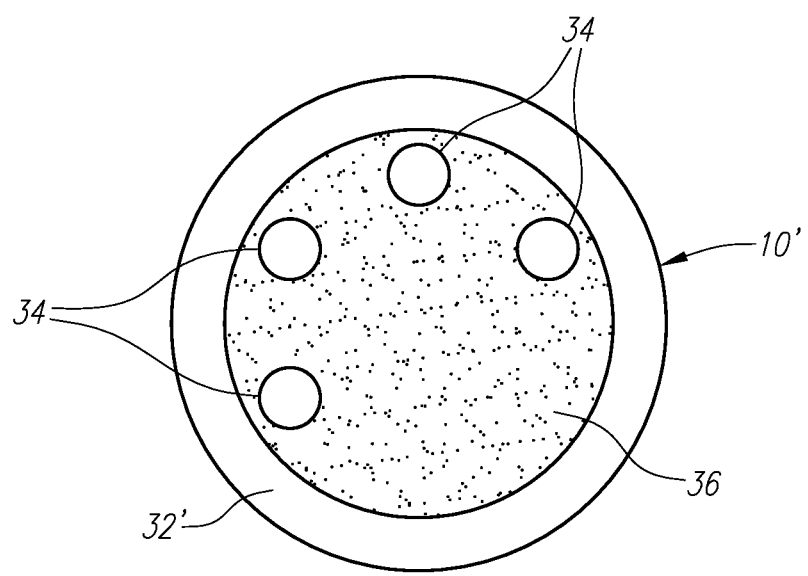
FIG. 1A schematically depicts an end view of a catheter having four capillaries potted therein.

As previously noted and as shown in FIG. 1, the AO flows antegrade with blood flow and exits from the distal end 30 of the capillary 20 (and, thus, the distal end 32 of the catheter 10) to mix with the blood. The catheter includes a bend 24 (or angle or joint) designed to help ensure that the AO 22 flowing from the distal end 30 of the capillary 20 does not impinge upon the aortic wall 18. In a catheter variation 10' that is shown in FIG. 1A, a group of capillaries 34 (for example, four) may be mounted in the catheter 10' in a substantially parallel configuration, with the distal ends of each capillary being potted in the distal end 32' of the catheter 10'. The number of capillary that may be mounted in this manner is limited only by the inner diameter (or 'ID') of the catheter and the outer diameter (or 'OD') of the capillaries.

FIG. 2 is similar to FIG. 1, but depicts an alternative catheter 210 designed for retrograde advancement within the aorta 12. In particular, a distal end 232 of this catheter 210 is closed or sealed (e.g., a portion of the sidewall may form the closed distal end of the catheter, or the distal end of the catheter may be sealed with, for example, a plug or an adhesive such as epoxy). The AO 22 would flow into the catheter 210 from the open proximal end and would travel toward the distal end 232 of the catheter 210 before entering the proximal end 28 of the capillary 20. The distal end 30 of the capillary 20 is mounted in the sidewall 38 of the catheter 210, as explained further below, such that the AO 22 exiting the capillary 20 flows antegrade. In this configuration, the catheter has multiple bends or curves 224, and the distal end 30 of the capillary 20 is mounted at a location in the sidewall 38 of the catheter 210 such that the AO 22 exiting the distal end 30 of the capillary 20 enters an obstruction-free zone or area (or fluid-delivery zone or area) created by the bends 224 such that the AO 22 does not immediately impact either the aortic wall 18 or another portion of the catheter itself. In particular, the curves 224 in the catheter depicted in FIG. 2 are configured to prevent the AO exiting the capillary 20 from impinging upon either the wall of the aorta or the wall of the catheter itself.

FIG. 3 is similar to FIGS. 1 and 2, but depicts a catheter 310 having a sinusoidal or sigmoid or serpentine configuration including a plurality of bends 324. This catheter is again adapted for retrograde advancement (i.e., in the direction of arrow 40) in the aorta 12 with antegrade AO flow. The distal end 332 of the catheter 310 is closed or sealed, and AO flows from the proximal end of the catheter toward the catheter's distal end (see arrow 42 representing AO flow direction in this embodiment). In the configuration depicted in FIG. 3, the sinusoidal configuration creates multiple obstruction-free areas or zones or locations for delivery of AO flow 22 into the bloodstream. In FIG. 3, three capillaries 20 are mounted in the inner lumen 326 of the catheter 310. To mitigate against excess interaction between streams emanating from adjacent capillaries, which could cause bubbling, the capillaries can be at least as close as 5 mm apart. Somewhere between 5 mm and 3 cm is a preferred separation between adjacent exit points (capillary distal ends). In addition to causing undesirable excess interaction between the stream of AO, spacing capillaries closer than 5 mm can undesirably affect the structural integrity of the catheter, at least when it is constructed from a polymer.

Each capillary has a proximal end 28 that may float freely in the catheter lumen 326, and a distal end 30 that is mounted in a sidewall 38 of the catheter at a location that enables the AO to flow antegrade from the capillary in substantial alignment with the direction of blood flow in the aorta. The number of capillaries that can be incorporated into a single catheter ranges from 1 to about 100, depending on the inner diameter of the capillary and the AO flow rate desired. For an oxygen concentration of 1 mL oxygen per gram physiologic liquid carrier (e.g., normal saline, lactated Ringer's solution (LR), D5W, or any combination of these), an AO flow rate of about 8 mL/min. to about 160 mL/min. can be provided with 1 to 20 capillaries having an inner diameter of 100 microns. If capillaries having an ID of 50 microns are used, about four times as many capillaries are required to achieve the same liquid flow rate at the same velocity.

An advantage of using smaller capillaries is that a higher concentration of oxygen can be stabilized. A 50 micron ID capillary can, for example, stabilize twice the concentration that a 100 micron capillary can stabilize. This advantage is at least partially offset by having to incorporate about four times as many capillaries, and the concomitant challenge in preventing small particulates from partially blocking the proximal end of very small capillaries (which can cause excessive microbubble formation). Also, the gas supersaturation threshold for nucleation varies inversely with the internal diameter of the capillary. For example, a 100 micron ID capillary can be used to predictably deliver water supersaturated with oxygen at 500 psi ($O_2$ concentration=1 mL $O_2$/mL water), while a 50 micron ID capillary will deliver bubbleless water supersaturated with oxygen at twice this $O_2$ pressure and concentration. The 50 micron capillaries can easily stabilize two cubic centimeters (cc) of oxygen per gram. The oxygen flow rate can range between, for example, 20-40 cc of oxygen per minute. With the use of submicron ID silica capillaries, the gas supersaturation threshold below the value required for nucleation is on the order of 1000 atm for oxygen and >2000 atm for helium, a gas with much lower solubility than oxygen. These values approach the theoretical limit for homogeneous nucleation and the tensile strength of water. Clearly, it is possible to use capillaries that are smaller than 50 microns (e.g., to help avoid volume overloading patients), but it can be difficult to prevent blockage and filtration.

For the 50 micron capillaries, a length of about 3 cm has been found to work well. Again, if the pressure in the capillary is doubled, then the capillary needs to be twice as long to maintain the same flow.

Figure 4:
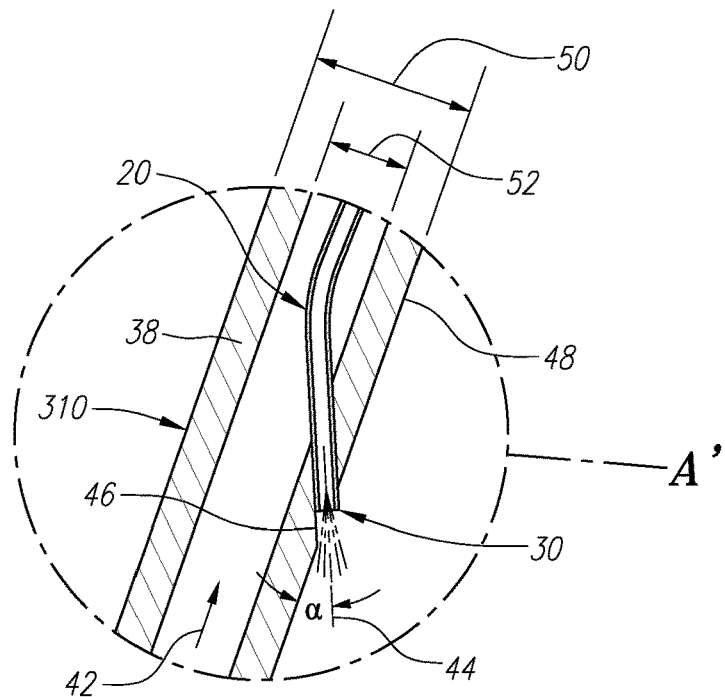
FIGS. 4 and 5 depict two variations (A' and A") of a greatly enlarged view of the circled area A of FIG. 3, and show a capillary mounted in the wall of a catheter.
Figure 5:
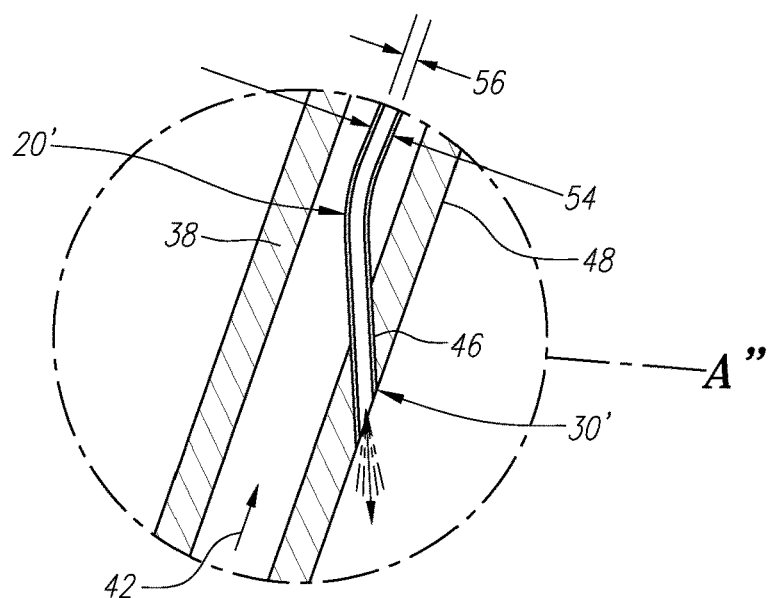

FIGS. 4 and 5 depict enlarged views of the circled portion A of FIG. 3, showing how the distal end 30 of a capillary 20 may be mounted in the sidewall 38 of a catheter. In FIG. 4, the capillary 20 distal end 30 has been cut transverse to the longitudinal axis 44 of the capillary. A corresponding channel or hole 46 has been cut or drilled through the sidewall 38 of the catheter. The distal end section or portion of the capillary has been advanced through the hole 46 through the catheter sidewall 38 and the distal end of the capillary 30 is substantially aligned with the outer surface 48 of the catheter sidewall such that AO exiting the capillary has a shallow delivery angle α relative to the longitudinal axis of the catheter. As shown in FIG. 4, the delivery angle α is the angle between the longitudinal axis of the capillary and the longitudinal axis of the catheter. The capillary 20 bends or deflects slightly before passing through the sidewall 38 the catheter. When the AO delivery angle α is kept shallow, the AO exiting the distal end 30 of the capillary can enter the blood flow while traveling in substantially the same direction as the blood flow. This helps reduce the potential for bubble formation. As may also be seen in FIG. 4, the catheter has and outer diameter 50 and an inner diameter 52. As shown to best advantage in FIG. 5, the capillary 20 similarly has a capillary OD 54 and a capillary ID 56.

Figure 5A:
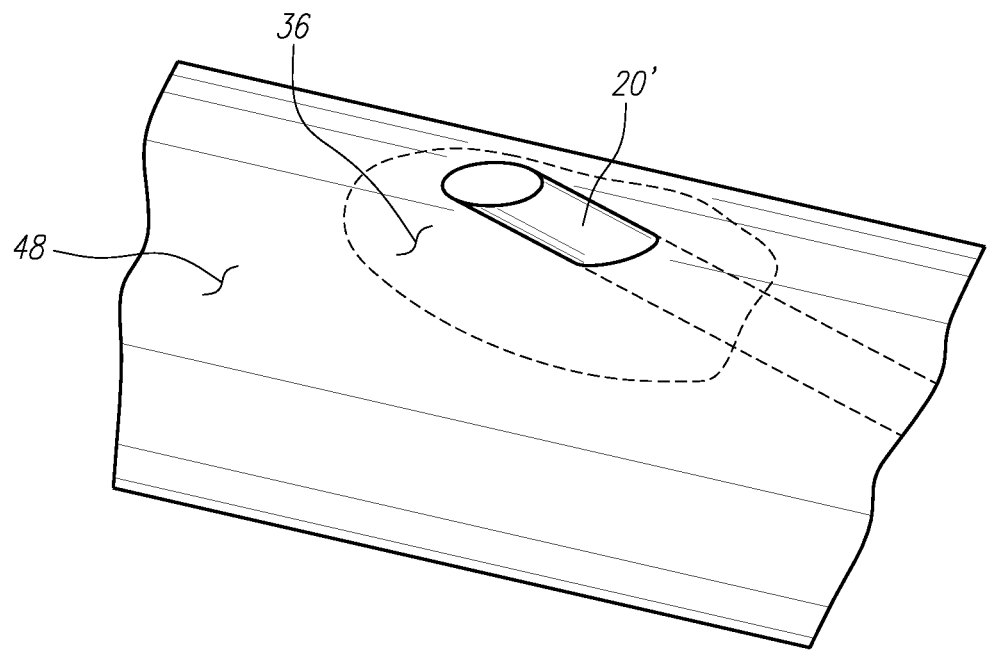
FIGS. 5A and 5B are enlarged, fragmentary views of a short section of catheter and schematically depicted possible steps for potting a capillary in a catheter sidewall.
Figure 5B:
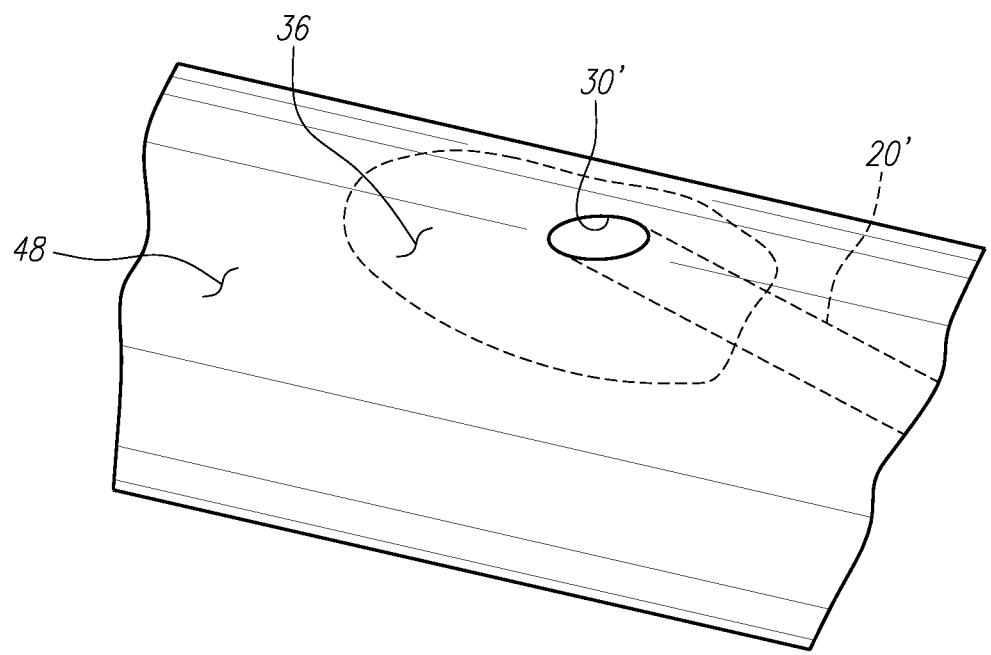

Referring most particularly to FIG. 5, an alternative configuration for the distal end 30' of the capillary 20' as it exits the catheter sidewall 38 is shown. In this configuration, the distal end 30' of the capillary 20' has been cut at an angle such that the surface transverse to the longitudinal axis of the capillary at its distal end may be mounted or potted substantially flush in the sidewall of the catheter. One way to achieve the configuration shown in FIG. 5 is to mount (for example, pot with epoxy 36 as shown in, for example, FIGS. 5A and 5B) a portion of the distal section of the capillary 20' in the sidewall 38 of the catheter such that it extends slightly away from the outer surface 48 of the sidewall 38 of the catheter by, for example, one centimeter. This intermediate configuration is depicted in FIG. 5A. After the capillary has thus been mounted in the catheter sidewall, the portion of the capillary extending away from the outer surface 48 of the catheter sidewall may be cleaved (e.g., with a diamond cleaver) and then ground down using, for example, a Dremel® tool manufactured by Robert Bosch Tool Corporation. Alternatively, an excimer (or exciplex) laser could be used to cut the distal end of the capillary so that the beveled geometry is in smooth continuity with the external surface 48 of the catheter. The catheter sidewall and the external surface of the capillary exit port may then be polished (e.g., with the Dremel tool), providing a completely smooth external surface of the catheter (as may be seen to best advantage in FIG. 5B) to ease passage of the catheter through sheaths and blood vessels; to avoid stagnant zones near the exit points, which could promote adhesion of platelets and growth of clots; and to reduce the number of possible nucleation sites.

In the catheter embodiments depicted in FIGS. 1-3, it may be possible for the AO effluent 22 to impinge upon either the wall 18 of a cylindrical vascular space, such as the aorta 12, or upon another portion of the catheter itself. However, as more curves (e.g. 24, 224, 324) are added (compare, for example, FIGS. 2 and 3 to FIG. 1), the catheter, along its length, is forced to become more centered in the cylindrical vascular space. The shape can be a 'gently' sinusoidal configuration (e.g., have a relatively-elongated sinusoidal configuration) to be effective in this regard (e.g., FIG. 3). The distal end of multiple capillaries may then be potted so that the AO effluent is delivered generally antegrade and away from the aortic walls.

Figure 6:
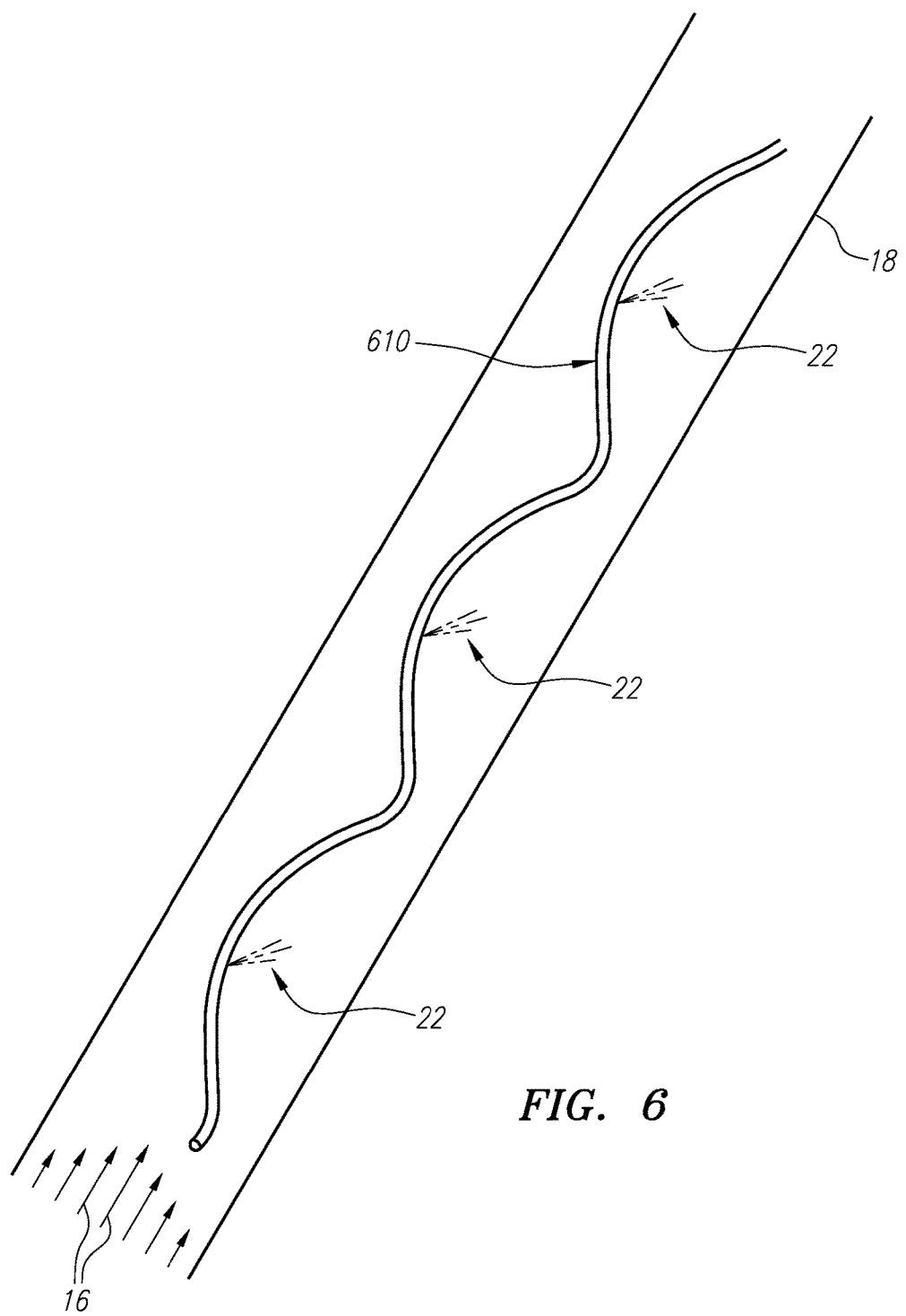
FIGS. 6-12 are highly schematic depictions of catheter configurations and AO delivery from various capillaries (not shown in detail) mounted in catheter walls so as to facilitate delivering AO in a manner designed to minimize bubble formation.
Figure 7:
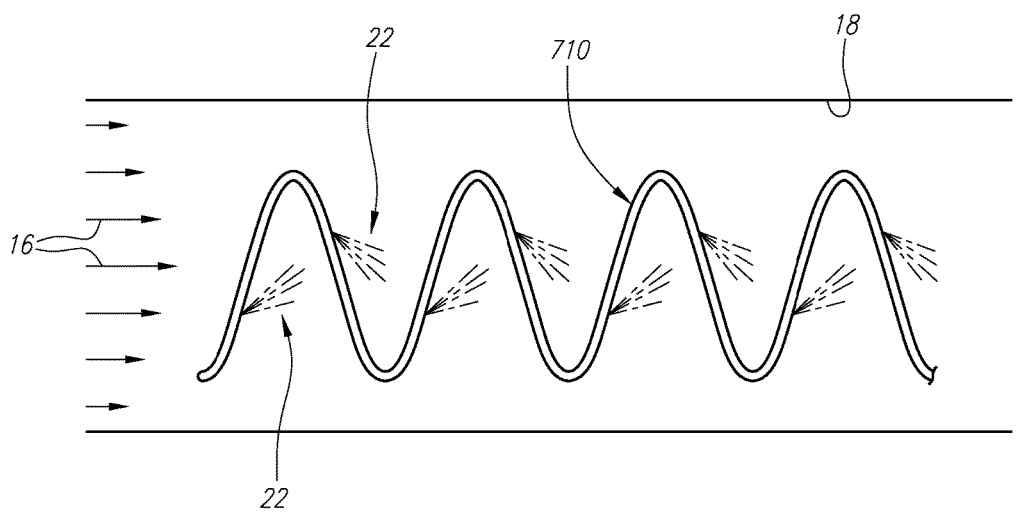

A helical shape (including near-helical shapes) is also advantageous for similar reasons. FIG. 6, for example, depicts a catheter 610 having 'gentle' helical configuration (e.g., a relatively-elongated helical configuration), which again creates a plurality of obstruction-free zones or areas or volumes (or fluid-delivery zones or areas or volumes) into which AO may be delivered. The shape depicted in FIG. 6 may also be referred to as a pseudo-sinusoidal or nearly-helical catheter configuration. A catheter according to the embodiment depicted in FIG. 6 may, for example, have a 5 French OD, with the diameter of the helix being approximately 1 cm. Three (shown in FIG. 6), four, or five silica capillaries, each approximately six inches long, with an ID of 100 microns, may be potted along the inner aspect of the helix, as shown in this figure, approximately 1-2 cm apart axially. The distal ends of the capillaries (not expressly shown in this figure) may be, for example, potted in the wall of a Radel® tubing in a direction that delivers the AO effluent 22 towards the obstruction-free volume at the center of the helix, away from the vessel wall, and generally antegrade with blood flow. Liquid flow rates of approximately 7 mL/min. per capillary are achievable with a driving pressure of 600 psi (achieved, for example, by increasing the oxygen gas pressure to this level in a 2 liter Parr pressure vessel filled with 1.5 liters of liquid and previously equilibrated with oxygen at 500 psi overnight). FIG. 7, depicts a catheter 710 having a 'more aggressive' helical configuration than what is depicted in FIG. 6. The entire core of the helical configuration could be thought of as a fluid-delivery volume or obstruction-free volume.

For simplicity, each of FIGS. 6 and 7 shows only the basic catheter shape and the AO exiting from the catheter sidewall. These figures do not show the corresponding capillaries. However, in these configurations, the capillaries are arranged such that their distal ends deliver the AO 22 toward the center of the blood vessel and, correspondingly, toward the centerline (or longitudinal axis) of the helical configurations 610, 710. Thus, the AO 22 is less likely to immediately impact a vessel wall 18 or another portion of the catheter 610, 710. That is, a potential advantage of the helical shape compared to the simple sinusoidal shape is that the AO effluent is not directed along the catheter long axis towards a nearby bend in the catheter. Under certain conditions (for example, when the cardiovascular fluid has a very high oxygen concentration), the AO effluent contacting downstream portions of a sinusoidal catheter before mixing of AO with blood is complete may cause bubble growth on the surface of the downstream portions of the catheters. This problem would not occur or would be greatly reduced with a helically-shaped catheter, where the AO 22 effluent can be directed towards the center of the helix and away from the catheter itself, as well as away from the walls of the aorta.

Figure 8:
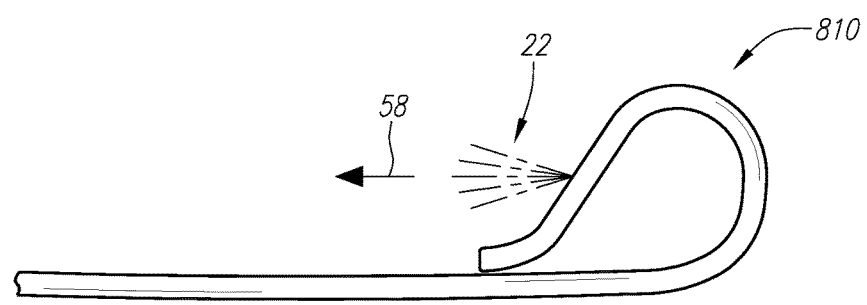
Figure 9:
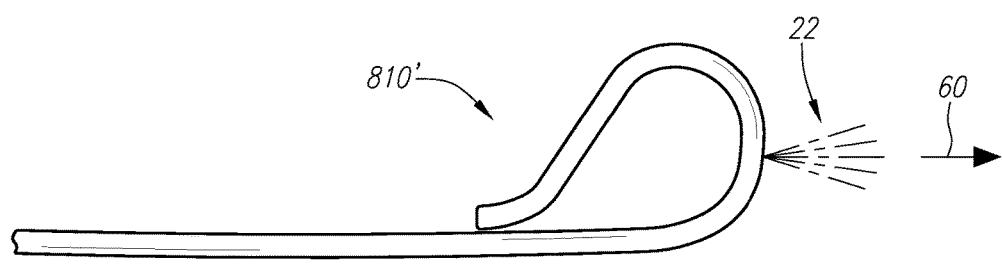

FIGS. 8-12 depict pigtail configurations for the capillary-carrying catheters. In each of these figures, a pigtail configuration is formed by doubling back upon itself a distal portion of the catheter. FIGS. 8 and 9 depict a first pigtail catheter 810, 810', respectively, where the distal end of the catheter actually points in the opposite direction and is substantially parallel to the longitudinal axis of the main catheter shaft. A capillary can be mounted in the distal portion of the catheter such that the AO flow exits in a desired direction, such as the first direction 58 depicted in FIG. 8 or the opposite, second direction 60 depicted in FIG. 9. Selection of the direction of flow for the exiting AO 22 would depend upon, for example, whether the catheter is being introduced antegrade (FIG. 9) or retrograde (FIG. 8) into the vasculature.

Figure 10:
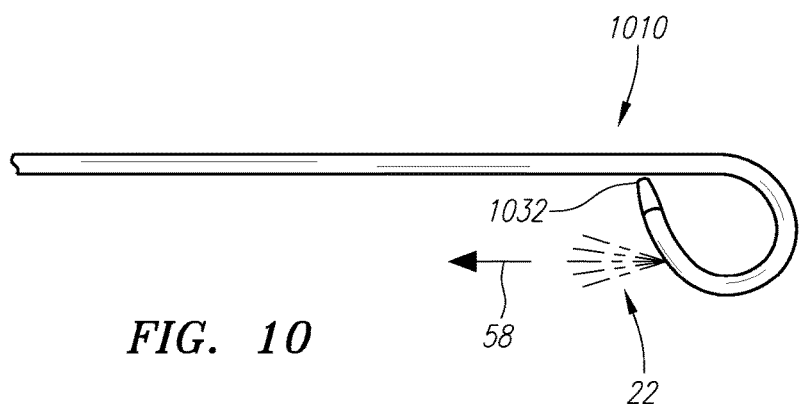
Figure 11:
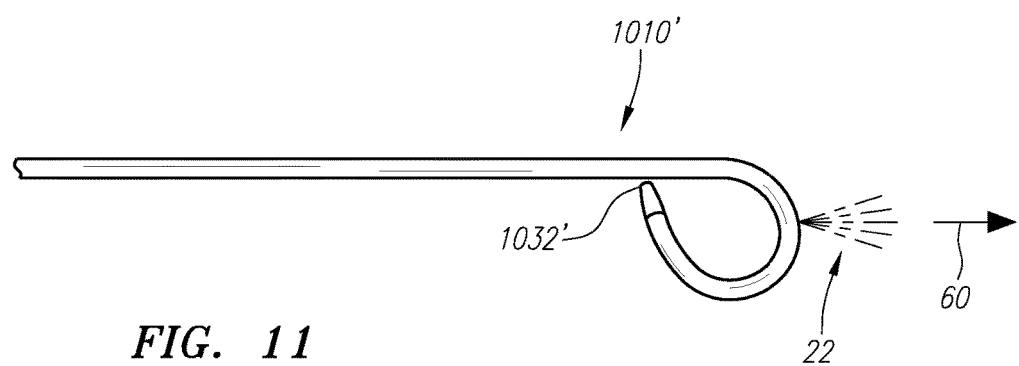

FIGS. 10 and 11 depict a second pigtail catheter 1010, 1010', respectively, where the distal end 1032, 1032', respectively, of the catheter is folded back onto itself. In this configuration, the AO 22 could again flow in alternative directions 58, 60 as shown. In particular, depending upon whether the catheter will be delivered antegrade (FIG. 11) or retrograde (FIG. 10), a capillary could be mounted such that the AO 22 flows in the first direction 58 shown in FIG. 10 or in the opposite, second direction 60 shown in FIG. 11.

Figure 12:
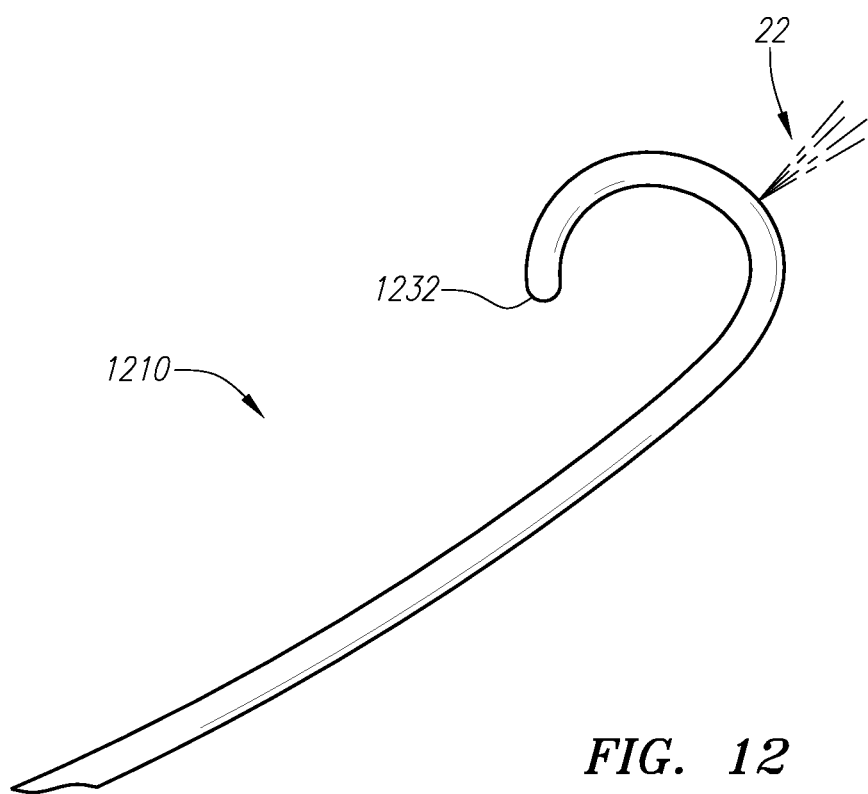

Finally, FIG. 12 shows yet another alternative pigtail catheter 1210. In this embodiment, the distal end 1232 of the catheter again folds back onto itself, but is not 'kinked' quite as hard as it is in the configuration depicted in FIGS. 10 and 11.

In the embodiment depicted in, for example, FIGS. 8, 9, and 12, a capillary could be potted in the distal end of the catheter, similar to what is depicted in FIGS. 1 and 1A.

In order to avoid excessive microbubble formation during mixing of the AO with blood flowing in a vascular space such as the aorta, it is important to rapidly (1-2 seconds) mix AO with blood upon exiting the capillaries over a time frame of several seconds. If the AO effluent is directed towards the solid surface of the vascular wall, such rapid dilution may not occur. Moreover, excessive turbulence incurred during mixing of AO with blood may also result in undesirable bubble formation. If the AO effluent is directed against blood flow (for example, retrograde infusion of AO), such turbulence is more likely to occur. Therefore, it is desirable to direct the AO effluent in the general direction of blood flow, away from the surface of the aortic wall. The catheter configurations depicted in FIGS. 1-12 are configured to achieve this objective.

There are numerous other potential catheter designs that could be considered to prevent the AO effluent from directly impinging upon the vascular wall. For example, if the AO is infused from the distal end of a straight catheter, the presence of a collar (not shown) near the distal end of the catheter would be helpful, as would an inflatable balloon or a flexible wire attachment, to reduce the opportunity for such impingement to occur. However, all of these latter designs increase the size and complexity of the catheter. Equally important, none of these designs allows for antegrade flow of AO when the AO delivery catheter is advanced retrograde up the aorta, such as from a common femoral artery approach.

Silica capillaries are currently thought to be the best type of capillaries to stabilize AO, since the internal surface is remarkably smooth at even the level of an atomic force microscope. They have a relative paucity of heterogeneous surface nuclei and are, therefore, useful for delivery of water highly supersaturated with oxygen into host liquids without bubble formation. At the proximal end 28 of the capillaries 20 (see, for example, FIG. 1), hydrostatic pressure is similar or greater than the dissolved gas partial pressure. At the distal end 30 of the capillary 20, the hydrostatic pressure is atmospheric, with no change in the high gas partial pressure. The fluid is, therefore, thermodynamically unstable, yet a phase change in the form of bubble nucleation in the capillary effluent requires extremely high levels of gas supersaturation because of the relative lack of nucleation sites on the silica surface. It is therefore a metastable liquid at gas supersaturation levels below a certain threshold. Capillaries made of other materials, such as PEEK (polyetheretherketone) tubing, Radel® tubing, and various metals (e.g., stainless steel or Nitinol, including electropolished metals), for a given internal diameter (e.g., 100 microns) currently do not predictably stabilize the same high level of oxygen concentration as fused silica capillaries.

Unfortunately, silica capillaries have a maximum useable radius of bending (before breaking) that precludes the 180 degree turn that would be required to infuse AO antegrade from the distal end of a catheter advanced retrograde up the aorta. For a typical application of AO with 1 mL $O_2$/g (600 psi driving pressure) infusion through a 100 micron ID silica capillary, lengths of 4 to 8 inches provide adequate flow below the threshold for turbulence within the capillary. Much shorter (e.g., 1 cm long), rigid capillaries could be potted at the distal end of a "pigtail" catheter, but the flow within the capillaries would greatly exceed the Reynold's number for the onset of turbulence. Shorter capillaries having a much smaller ID could be considered, but a much greater number of such capillaries would have to be used to achieve the same AO flow rate. For example, for a given flow velocity, 16 capillaries, each with a 25 micron ID and length of about 1 cm would be required to achieve the same flow rate as a single 6 in. long 100 micron ID capillary. Glass capillary arrays are available commercially, but closely spaced capillaries can produce microbubbles from solid surfaces between adjacent flows. In addition, filtration to prevent blockage (with bubble formation) of smaller capillaries is much more challenging than the use of the 100 micron ID capillary. A single particle that partially blocks one capillary can produce a large number of microbubbles from the end of the capillary.

It should also be kept in mind that the working pressure is directly proportional to the length of the capillaries if it is desirable to maintain the same flow rate. If you doubled your working pressure then you would have to double the length of the capillaries to have the same flow rate.

As shown in FIGS. 1-12, the combination of the catheter shape and the orientation of the distal ends of the capillary tubing potted in the catheter control the direction of the AO effluent from the catheter, relative to the direction of blood flow in a vascular space such as the aorta. A minimum requirement is the presence of a gentle curve near the distal end of the catheter, with the distal end of a capillary potted at or near the distal end of the tubing. For AO flow that is antegrade with respect to vascular blood flow when the catheter is advanced antegrade (e.g., from the radial artery into the aorta), the distal end of the capillary can be potted within the lumen at the distal end of the capillary or potted within the wall close (e.g., a few millimeters) to the end of the catheter (FIG. 1). When this catheter is advanced retrograde (e.g., from the femoral artery), AO flow will also be retrograde and suboptimal. However, by potting the distal end of the capillary in the opposite direction in the wall of the catheter, the AO flow will then be generally antegrade with respect to blood flow in the aorta when the catheter is advanced retrograde from the femoral artery (FIG. 2).

In one embodiment, three foot lengths of Radel-R tubing (e.g., Upchurch Scientific tubing available from the IDEX Health and Science unit of IDEX Corporation) having an outer diameter of approximately 0.0625" (i.e., 1/16") and an inner diameter of either 0.020", 0.030", and 0.050" have been used for the body of the catheters (one 3 foot length per catheter). The tubing as provided from the manufacturer is somewhat curved after removal from spools. The tubing is translucent, a property useful for internal inspection. It also has a high burst pressure rating, on the order of 7,000 to 12,000 psi, well above the typical maximum working pressure of 1,000 psi for the AO catheters. Moreover, the material is biocompatible in terms of potential clinical applications and it is hydrophilic, so that bubble nucleation along its surface is retarded. Finally, it is easily thermally shapeable without compromising its mechanical properties. In order to shape a length of Radel tubing, it is placed within 0.25" OD copper tubing (thick walled), which had previously been shaped into a helical form by winding it around a 0.25" steel rod. The Radel tubing within the helical copper tubing is then heated for a few minutes, either with a heat gun or by simply placing it within an oven at 210 to 250 degrees F. followed by cooling to room temperature, to yield a helical shaped Radel tubing.

Small holes are then drilled at approximately 1 cm axial intervals along the inner aspect of the helical Radel tubing. A micromanipulator may be used to advance a micro-drill bit (typically 0.076" to 0.086" diameter) at a 20 to 30 degree angle, relative to the tubing surface, through the sidewall of the tubing. The angle of entry is also adjusted radially so that the long axis of the hole points towards the center of the helix formed by the catheter. Typically, three to five holes are drilled in order to accommodate the same number of 100 micron ID capillaries which, together, can provide sufficient AO flow (approximately 15 to 35 mL/min. with AO=1 mL $O_2$/g saline) to hyperbarically oxygenate arterial blood flowing at 2-3 liters per minute in the aorta.

After cleaning and sonication while flushing with distilled water, the tubings are dried with clean compressed air. Silica capillary tubings (e.g., 100 micron ID, 265 micron OD tubings available from Polymicro Technologies) are carefully cleaved rotationally with a diamond cutter to a predetermined length, typically 4" or 6", and are cleaned and dried. As previously mentioned during the above discussion of FIGS. 5A and 5B, each length is threaded through a hole made with the micro-drill bit, such that a few millimeters protrude outside the external surface of the tubing. A glue/ adhesive is allowed to wick into the space between the silica tubing and wall of the Radel tubing. Following curing of the glue/adhesive (either time for the glue or UV/white light for the adhesive), the portion of the silica tubing protruding outside the Radel tubing is cleaved off, and the remaining glue/epoxy is shaved/polished off with appropriate tools (e.g., a Dremel tool).

A high pressure fitting (e.g., one from Upchurch Scientific) is attached to the proximal end of the Radel tubing. After a final cleaning/rinsing step, the distal end of the Radel tubing is sealed with glue or adhesive.

Prior to delivery of AO, the catheter is rinsed with alcohol to help eliminate gas-filled nucleation sites (microscopic and submicroscopic crevices) and flushed with distilled water. The transition from distilled water to AO is performed in a manner to prevent re-seeding such crevices with microscopic/submicroscopic gas pockets.

Each AO catheter may be tested in a 30 gal. aquarium filled with room temperature tap water. An ultrasound probe may be immersed under the water to inspect the AO effluent from the catheter for the presence of microbubbles emanating from the distal end of the catheter. If no bubbles are noted, the catheter is deemed suitable for use.

Oxygenation of the Carrier Liquid

A physiological carrier liquid, such as normal saline, D5W, lactated Ringer's solution, plasma, a colloid preparation such as hetastarch or 5 g % albumin, or various formulations or combinations of similar solutions, is pressurized with oxygen so that the carrier liquid contains an oxygen concentration of at least 1 mL $O_2$ per gram of liquid upon decomposition at or near atmospheric pressure and a temperature ranging between 0 and 40 degrees Celsius.

There are many methods to dissolve oxygen in the carrier liquid (for example, mixing oxygen gas with water with a magnetic mixer or a impeller/stirrer in the water; sparging or bubbling gas through the liquid; releasing gas from a precursor such as hydrogen peroxide and a catalyst). However, a method that provides a hydrostatic pressure that is higher than the dissolved oxygen pressure is desirable. Most of the methods rely on exposing the carrier liquid to oxygen gas at a sufficiently high pressure to achieve the desired $O_2$ concentration at room temperature. For most carrier fluids, an oxygen gas pressure of 500 to 600 psi is adequate to achieve a dissolved $O_2$ concentration of 1 mL $O_2$/g fluid. A roughly linear relationship exists between the oxygen gas pressure and the oxygen concentration in the liquid exposed, so that doubling of the gas pressure will result in a doubling of the dissolved $O_2$ concentration in the carrier liquid. However, it should be recognized that, as the target dissolved $O_2$ concentration increases between 1 mL $O_2$ and 4 mL $O_2$/g carrier liquid, the rate of oxygen diffusion into the liquid decreases, resulting in longer periods of time for equilibration of the dissolved oxygen partial pressure with the gas phase oxygen pressure.

Among the methods for exposing the carrier liquid to oxygen gas, rapid mixing of the liquid with either a magnetic stirring bar (Teflon-coated to avoid rust formation) or a propeller-type stirrer (magnetically coupled as used in standard Parr Reactor pressure vessels) is simple and allows >90% completion of the equilibration $O_2$ concentration in the liquid in 1-2 hours for a 2 liter capacity pressure vessel. An alternative method consists of spraying the liquid as a fine mist into a vessel pressurized with $O_2$ gas and maintained at the desired level of gas pressure, with the fine droplets coalescing with gravity to form a continuous liquid level at the bottom of the vessel. With both types of approaches, a dip stick or stem near the bottom inner surface of the pressure vessel allows the carrier liquid with the dissolved oxygen to flow from the vessel, upon opening a valve, to a tubing that is in liquid communication with the catheter.

Delivering the Oxygenated Carrier Liquid to the Catheter

Figure 13:
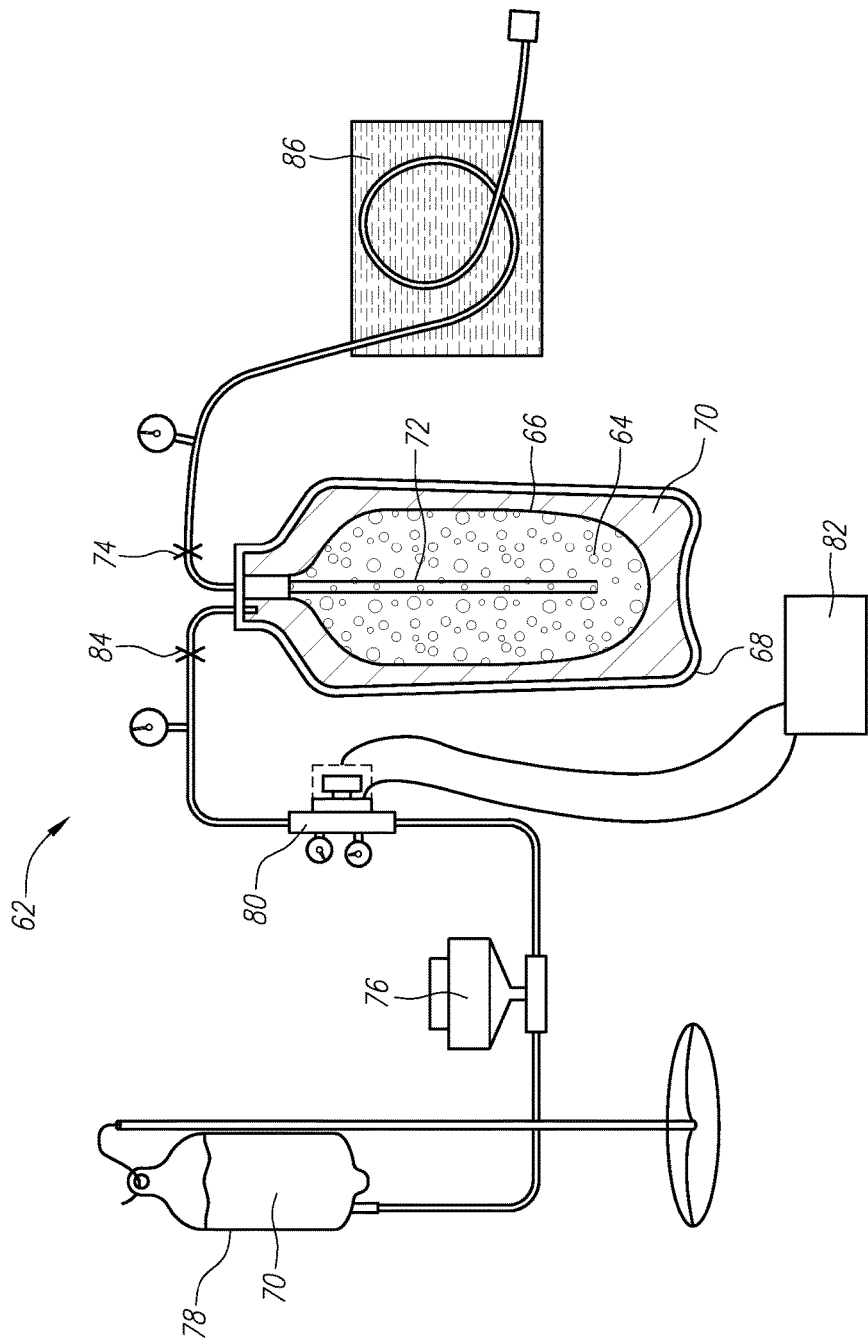
FIG. 13 depicts one possible system for delivering a cardiovascular fluid (e.g., supersaturated saline) for use in the disclosed catheters.

It should be apparent that there are several methods of delivering the carrier liquid 64, oxygenated at the desired gas concentration, to the proximal end of the catheter. FIG. 13 depicts one possible system 62 for delivering a cardiovascular fluid (e.g., supersaturated saline) 64 for use in the disclosed catheters. This figure shows a system 62 for providing oxygen already dissolved at high pressures (e.g., 1 mL/g aqueous solution or greater concentration) to the AO catheter. Also, FIG. 13 depicts a system 62 for supplying AO in a batch mode, but it is possible to supply the AO to the catheter in a continuous mode.

In this system, the oxygenated liquid 64 (e.g., physiologic liquid with oxygen dissolved at ≥1 mL $O_2$ per gram of liquid) is maintained in a gas-impermeable container 66, such as an aluminized polymer bag suspended within a pressure vessel 68 (e.g., one available from the Parr Instrument Company), after venting the gas phase. The container is similar to commercially available containers (e.g., "bag in can" technology available from CCL Container), but the pre-pressurized material 70 is, preferably, a physiologic liquid rather than a gas. A gas, such as oxygen or an inert gas, could be used if one could ensure that the gas could not permeate through the container 66 holding the oxygenated liquid, but a gas is not going to respond to sudden changes in pressure as well as a liquid. It should also be noted that, as an alternative to the polymer bag 66, a collapsible accordion-type metal container or even a metal bag could be used, particularly if the moving parts were comprised of a flexible metal such as Nitinol. Application of pressure outside the bag can then be used to drive the oxygenated carrier liquid 64, at a hydrostatic pressure greater than the dissolved oxygen partial pressure, from the bag to the catheter via a dipstick or stem 72 within the bag (upon opening a suitable valve) 74.

As noted above, the source of pressure (e.g., a pressure ≥the desired dissolved gas pressure) to the AO within the gas-impermeable bag or accordion-type metal enclosure is a liquid, such as water (e.g., distilled $H_2O$), delivered under pressure from a hydraulic pump 76. The hydraulic pump may, for example, be an air-operated pump. Such pumps are inexpensive and are capable of providing a step-up in pressure from a bag 78 of saline or other physiologic solution at ambient pressure to incredibly high hydrostatic pressures (e.g., even greater than 50,000 psi if desired) in an automatic manner without electrical controls, with the simple use of air pressure at a pre-set level and two one-way ball valves on either side of the pump. In order to ensure smooth transitions in hydrostatic driving pressure from the pump 76 to the fluid 70, a standard method may include a pressure wave dampener (not shown) with a suitable frequency response that can be interposed between the two.

The advantage of driving the oxygenated carrier liquid (AO) at a higher hydrostatic pressure than the dissolved gas pressure is that the stability of the liquid, in terms of bubble nucleation, is better ensured during passage (which could be turbulent) through valves and connections. It is also important in this regard that the hydrostatic pressure does not fall below the dissolved gas partial pressure upon entry into the proximal end of the catheter. Moreover, if there are multiple capillary tubings mounted at different axial locations along the shaft of the catheter, the hydrostatic pressure at the entrance of each capillary may not be uniform. To ensure that an excessive pressure drop in hydrostatic pressure does not occur at the entrance (proximal end) of any of the capillaries, use of a suitably high hydrostatic pressure could be applied to the flexible container 66.

Rapid mixing of AO with blood (1-2 seconds) is critical to prevent excessive local increase of the level of oxygen supersaturation of AO with blood. Blood flow is naturally phasic, with most of the flow occurring during systole (cardiac contraction). If diastole is long (for example >1 sec), the local level of oxygen supersaturation may exceed 3 atm, which could produce an excessive number of microbubbles. Therefore, it is desirable to be able to coordinate the AO infusion into the aorta with the arterial pulse wave. By raising the hydraulic pressure to a level greater than the dissolved oxygen pressure, it is practical to deliver AO during both systole and diastole without lowering the hydrostatic pressure to a level that is lower than the dissolved gas pressure. A preferred level of hydrostatic pressure would be about 2-3 times higher than the dissolved gas pressure to achieve this effect.

Liquid pressure and liquid flow regulators 80 are commercially available to adjust the pressure or flow of liquid 70 downstream from the regulator, with inputs under computer control 82 from one or more sources (for example, see Tescom regulators/control systems). The ECG or arterial pressure waveform from a patient can be used to provide such signals, similar to the synchronization used to operate the performance of an intra-aortic balloon pump catheter. Another input signal that can be incorporated in control of the regulator would be the arterial $PO_2$ distal to the location of AO infusion. If the $PO_2$ exceeds 850 mmHg, the AO flow rate can be reduced, so that the chance of excessive microbubble formation can be avoided. In addition, the detection of excessive microbubbles (for example, signals from an intravascular ultrasound device or an intravascular fiber optic bubble detector mounted on the shaft of the AO catheter) could be used to stop AO infusion via the regulator 80 or a separate cut-off valve 84.

With the use of either a pressure regulator or flow regulator, which is controlled by the computer 82 receiving either the ECG signal or arterial waveform (similar to an intra-aortic balloon pump catheter), the AO flow rate can be varied during the cardiac cycle. During systole, when blood flow in the aorta is greatest, the AO flow rate can be made to be higher than during diastole, when aortic flow may be stagnant. As already noted, the phasic matching of the AO flow with the blood flow would help in reducing the potential for causing transient, excessive increase in supersaturation levels of oxygen and resultant potential problems with excessive microbubble formation. An alternative approach that is helpful is simply having a heart rate that is sufficiently rapid to decrease excessive periods of stasis during diastole. For example, a heart rate that is at least 60 beats/min. appears to be adequate to achieve hyperbaric oxygen levels in the aortic blood flow without excessive bubble formation.

The AO delivery system 62 shown in FIG. 13 also incorporates an optional cooling reservoir (or cooling loop) 86 proximal to the AO catheter. By cooling the AO liquid, the stability of the AO can be increased since the solubility of oxygen increases with decreasing temperature. If the AO is cooled to approximately 2 degrees C., the maximum level of oxygen supersaturation concentration of AO for a given capillary ID can be increased by about 50%. Thus, for a 100 micron ID capillary, the maximum level of AO to ensure bubbleless delivery into blood can be increased to about 1.5 mL $O_2$/g liquid compared to 1.0 mL/g at room temperature. Cooling the AO may also be particularly helpful when treating, for example, shock or patients with cardiac arrest.

In addition to the use of flexible containers 66 to house the oxygenated carrier solution, it should be apparent that a cylindrical pressure vessel with a piston-type apparatus could be used. After oxygenating the carrier solution, the gas phase could be vented through a valve by driving either a cylindrical plug (such as a metal cylinder with O-ring seals) or a cylindrical drive shaft that applies the desired level of hydrostatic pressure.

Other factors are also important to avoid bubble formation during infusion of physiologic solutions such as saline supersaturated with oxygen ("aqueous oxygen" or AO) into host liquids such as blood. Excessive turbulence during mixing of the two liquids can result in bubble formation initiated within the relatively low pressure center of flow vortices. Flow velocities that exceed the Reynold's number (a dimensionless value) of about 2000 to about 2200 within the capillary also incur the risk of bubble formation within the capillary. Therefore, AO flow velocities are chosen so that flow is laminar within the capillary. In order to avoid excessive turbulence during mixing of AO with blood, the maximum $O_2$ concentration of AO below the threshold for nucleation will be increased by delivering AO in the same direction as blood flow. In addition, rapid (about several seconds) dilution of the AO with blood to an equilibrium oxygen partial pressure value below about 3 atm needs to be accomplished to prevent bubble formation in blood.

Figure 14:
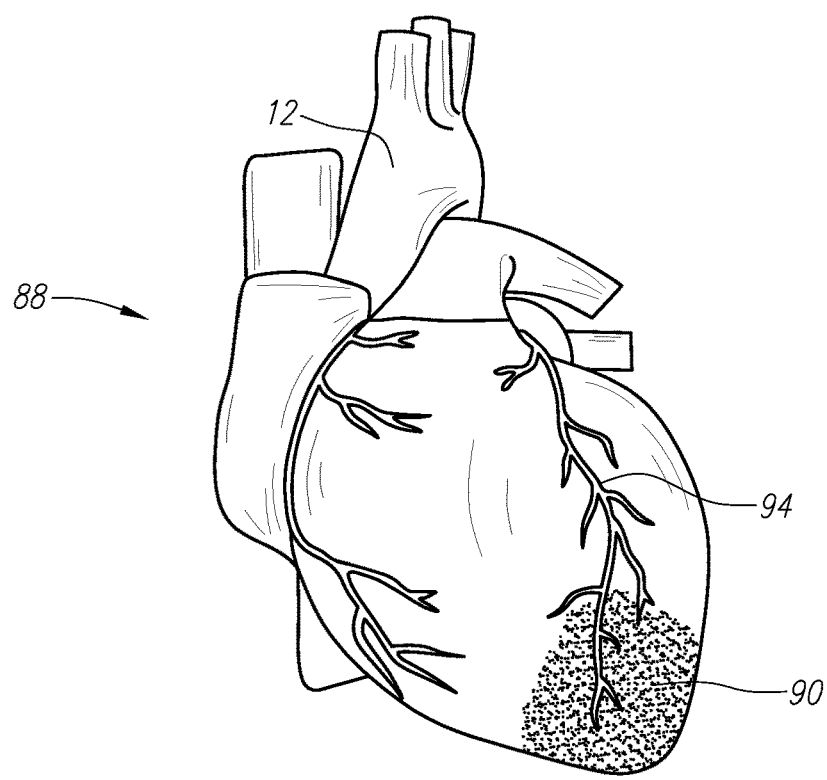
FIG. 14 is an isometric view of a heart with an infarct.
Figure 15:
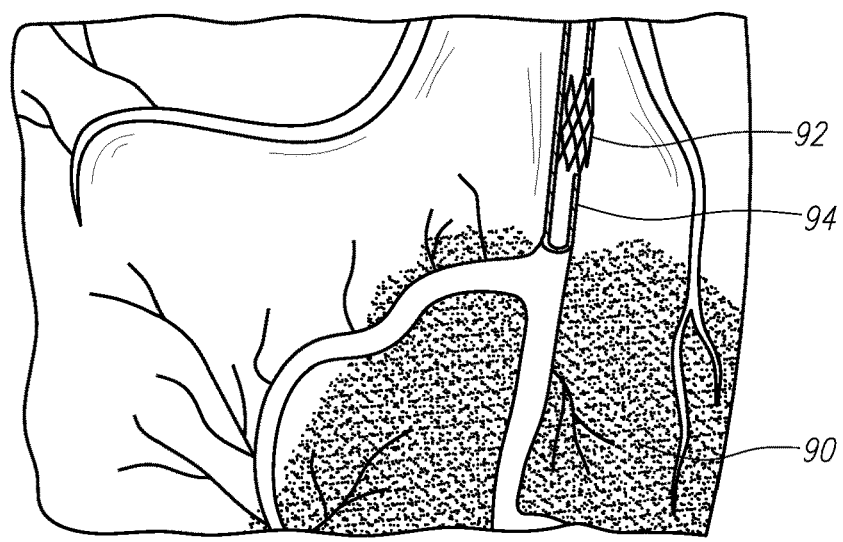
FIG. 15 is an enlarged view of a portion of FIG. 14, but also showing a stent being delivered upstream from the infarct.

FIGS. 14 and 15 relate to one possible use of the disclosed catheters. In particular, FIG. 14 depicts a heart 88 after suffering a heart attack and having an infarct 90. One option for treating a heart attack is prompt balloon angioplasty and stenting known as percutaneous coronary intervention (PCI). In FIG. 15, a stent 92 is being placed in the left anterior descending coronary artery 94. The stent reopens the blocked artery, but the patient may continue to suffer from heart muscle damage resulting from prolonged lack of oxygen. The AO deliverable via the disclosed catheters may be used to treat and help heal the damaged cardiac tissue.

Figure 16:
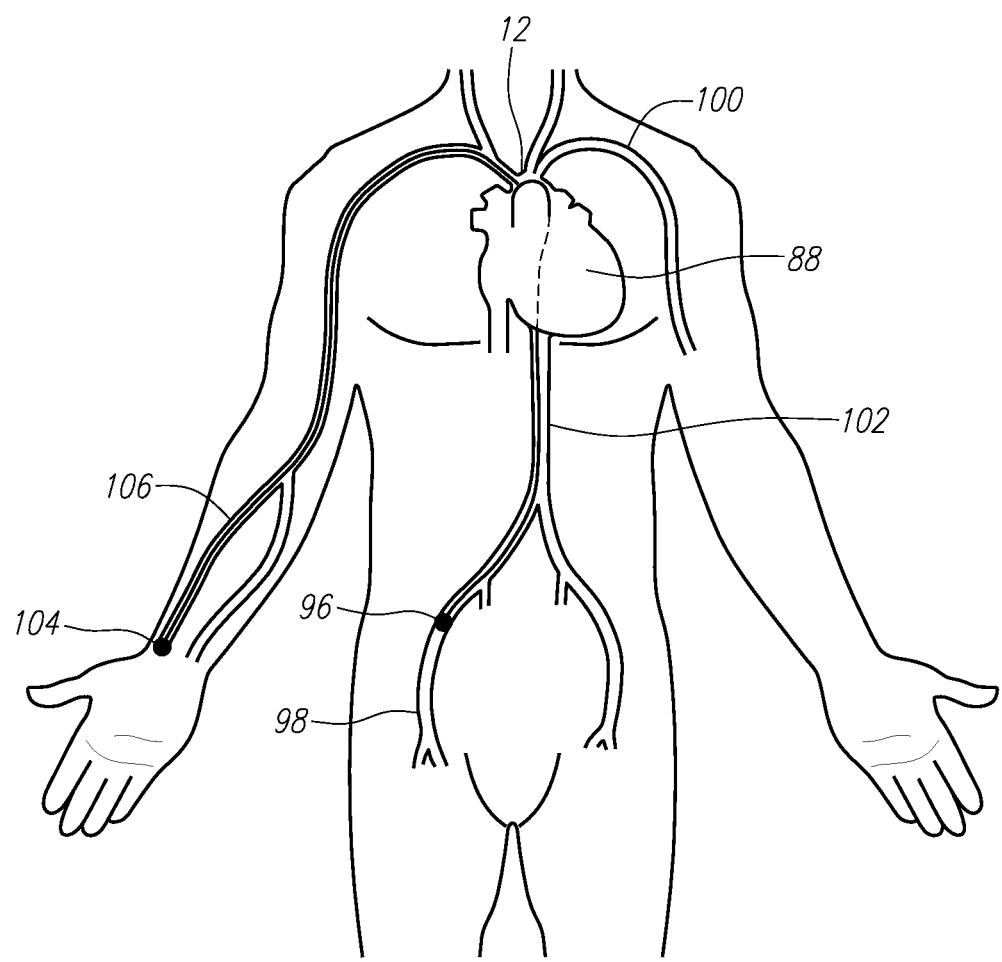
FIG. 16 schematically depicts possible options for navigating a catheter according to the present invention to an area to be treated.
Figure 18:
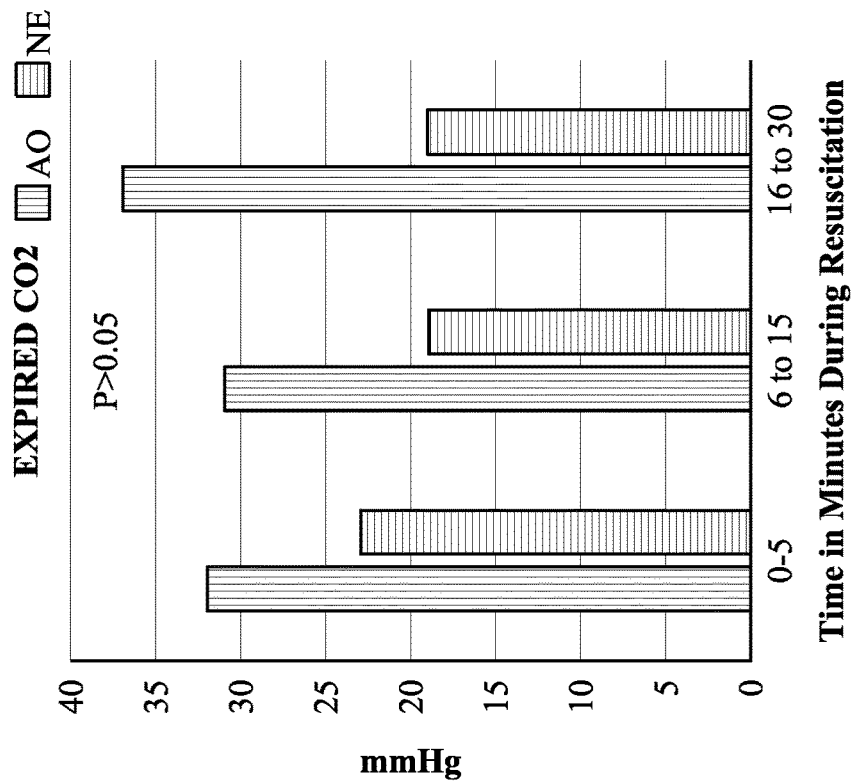
FIG. 18 is a bar chart showing end-tidal $CO_2$ (in mmHg) as a function of resuscitation time (in minutes), and includes bars for treatment with aqueous oxygen and for treatment with norepinephrine.

Typically, a catheter is deployed and manipulated through a patient's vasculature to the intended treatment site, for example, a site within a patient's aorta 12. FIG. 16 schematically depicts two possible paths for navigating a catheter according to the present invention to the aorta 12. The simplest method for delivering AO is to insert the catheter retrograde (e.g., approaching from an entry point 96 in the right femoral artery 98) into the aorta, with AO flowing antegrade through the capillaries (see, for example, the catheter configuration shown in FIG. 2). For example, the oxygen therapy could be performed with the distal end of the catheter located just past (moving toward the heart 88) the left subclavian artery 100, so that it sits around the beginning of the descending thoracic aorta 102. As also shown in FIG. 16, it is also possible to position a catheter for delivery of AO by advancing the catheter in an antegrade manner into the descending aorta from, for example, an alternative entry point 104 on the right (or left) radial artery 106. This latter approach may be advantageous in patients with severe peripheral arterial disease.

It should be apparent that the present invention could also be used for many other medical applications, including virtually any condition characterized by tissue hypoxia not correctable by breathing or ventilation with oxygen gas. Such conditions include blockage of blood vessels (e.g., myocardial infarction and stroke) for increasing oxygen to tissues via collaterals; reperfusion states wherein microvascular flow is inadequate; systemic hypoxia from pulmonary problems; severe pulmonary hypertension; hypoxic tumors that are resistant to radiation therapy; and severe infections wherein blood flow is poor or immune function is impaired.

Although use in an aorta is discussed above, it should also be apparent that the present invention could be used to deliver aqueous oxygen to locations other than the aorta. For example, the catheter described herein can be used to infuse AO into the inferior vena cava (IVC). In one example, a 5 French catheter with four capillaries (e.g., each capillary being four inches long and having an ID of 100 microns) may be advanced through a femoral artery sheath in a femoral vein to the upper IVC. Such a catheter can deliver, for example, 25 mL oxygen/min. into the IVC for as long as 15 minutes without microbubble formation as monitored with transesopheal echo (TEE) in an anesthetized juvenile domestic swine model. The advantage of the venous approach is that it would allow placement of a catheter for prolonged period of oxygen support, even weeks, and facilitate treatment of numerous lung problems such as pulmonary hypertension, pneumonia, and pulmonary emboli.

Treating Hemodynamic Shock Associated with Critical Anemia

The catheter disclosed herein may also be used effectively to treat hemodynamic shock associated with acute isovolemic critical anemia. In particular, during isovolemic exchange transfusion with LR, hemodynamic shock (HS) occurs rapidly at a [Hb]<3 g %. Intraaortic (IA) infusion of AO can be used to achieve hyperbaric arterial $O_2$ tensions in plasma and, thereby, to attenuate tissue hypoxia associated with low erythrocyte flow. IA-AO improves mean arterial pressure (MAP) and end-tidal $CO_2$ (Et-$CO_2$) in a swine model of HS.

In a study, juvenile domestic swine weighing 30+/−5 kg were intubated, anesthetized with isoflurane, and ventilated with 35% $FiO_2$. After establishing a two hour stable hemodynamic baseline, rapid blood exchange was performed with LR over the next hour in a ratio adequate (approx. 1:1.2) to maintain central venous pressure (CVP) of 2-8 mmHg (n=10) while reducing [Hb]<3 g %, resulting in shock, defined as MAP and Et-$CO_2$ both <25 mmHg. In the AO group (n=5), AO was delivered through a 5 F catheter into the descending aorta at 30 mL $O_2$/min. intermittently for 1-2 min., at 5-8 min. intervals for 25 min. In the NE group (n=5), NE was infused i.v. at 48 mcg/min. Epinephrine 1 mg i.v. was co-administered with NE if asystole occurred. Transesophageal echo (TEE) was performed throughout, and blood samples obtained for blood gas analysis (iStat).

Figure 17:
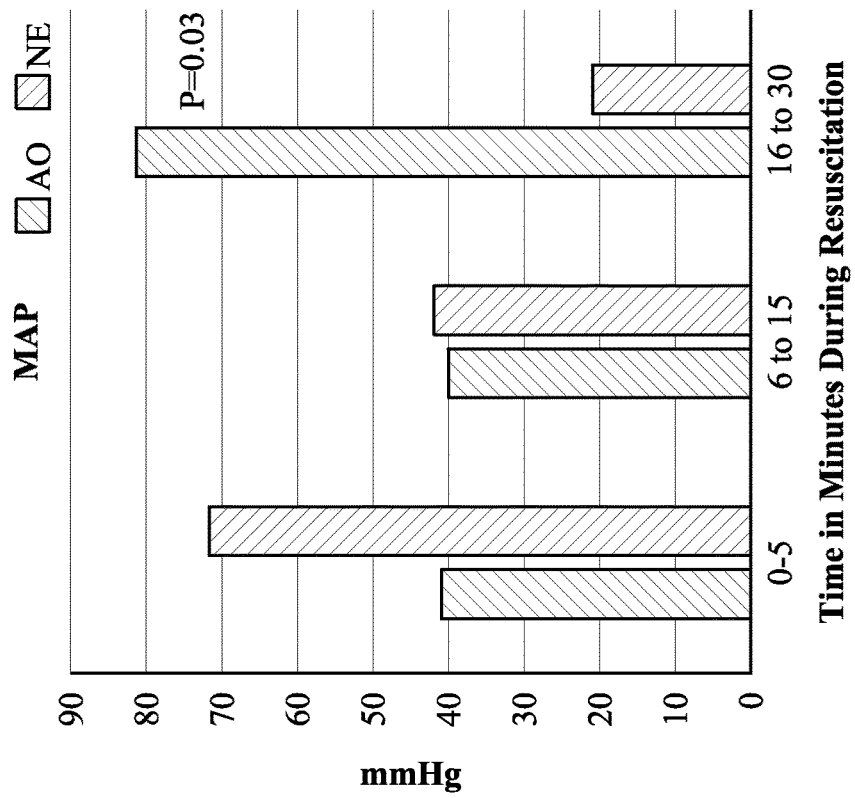
FIG. 17 is a bar chart showing mean arterial pressure (in mmHg) as a function of resuscitation time (in minutes), and includes bars for treatment with aqueous oxygen and for treatment with norepinephrine.
Figure 19:
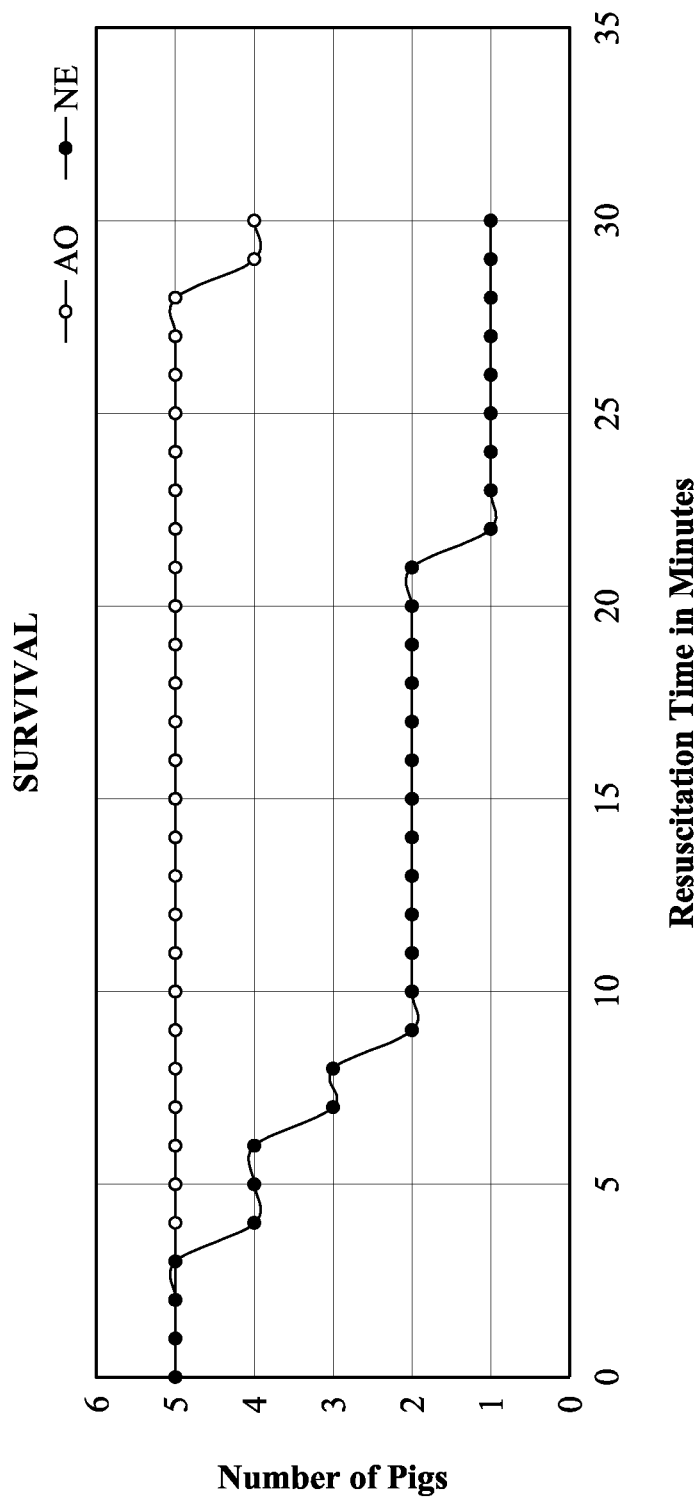
FIG. 19 is a line chart showing survival rate (in number of pigs) as a function of resuscitation time (in minutes), and includes a first line for treatment with aqueous oxygen and a second line for treatment with norepinephrine.
Figure 20:
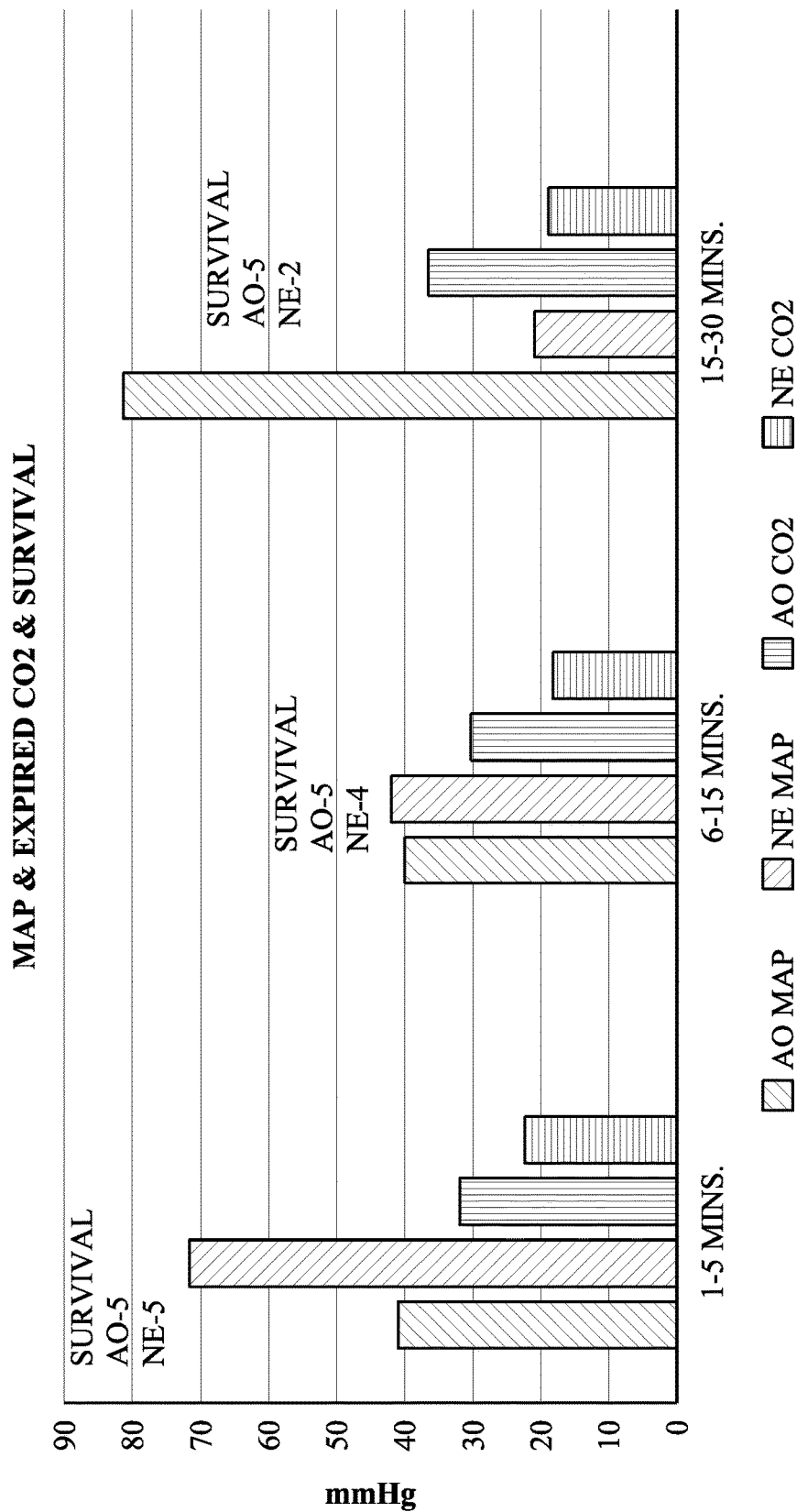
FIG. 20. is a bar chart that consolidates data from FIGS. 17-19.

As shown in a FIGS. 17 and 20, in the first 5 min. of resuscitation, MAP was significantly improved (p<0.01 compared to baseline values) in both groups. However, MAP fell significantly over the next 10 min. only in the NE group (p<0.05). Mean Et-$CO_2$ in the NE group was significantly lower compared to the IA-AO group throughout resuscitation (p<0.05). As shown in FIGS. 19 and 20, survival at 25 min. of resuscitation was significantly greater for AO (100%) than for NE (40%). Mean cardiac out by echo was greater for AO (3.2 L/min) versus NE (2.0 L/min) at 10-25 min. of resuscitation.

Based on this study, and as shown in FIGS. 17-20, IA-AO infusion is more effective than i.v. NE in treatment of hemodynamic shock in this model.

Additionally, infusion of gas-supersaturated fluids can be used diagnostically for enhancing imaging of cardiovascular spaces and perfused tissues. As examples, infusion of oxygen microbubbles into a cardiovascular space could be used to enhance echo contrast; carbon dioxide microbubbles could be used for angiographic (x-ray) imaging; and hyperpolarized helium-3 gas bubbles could be used to enhance magnetic angiographic imaging.

Embodiments are described herein of various apparatuses, systems, and/or methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of all embodiments.

For example, both the catheter tubing and the capillary tubing may be made out of Nitinol. A helical Nitinol catheter could, for example, be configures so that it is helical only at body temperature, and at room temperature goes back to a straight tube. The user could flush the Nitinol catheter with room temperature saline while inserting it into a patient to keep it straight. The catheter would automatically turn into a helix in the body during use. When it came time to remove the catheter, the user could again flush it with cold saline to straighten the catheter to facilitate extraction. Further, if Nitinol capillaries were soldered into a Nitinol catheter, the whole catheter would have a high burst rating, making it very safe to use.

Reference throughout the specification to "various embodiments," "some embodiments," "one embodiment," "an embodiment," or the like, means that a particular feature, structure, or characteristic described in connection with the embodiment(s) is included in at least one embodiment. Thus, appearances of the phrases "in various embodiments," "in some embodiments," "in one embodiment," "in an embodiment," or the like, in places throughout the specification, are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features, structures, or characteristics of one or more other embodiments without limitation given that such combination is not illogical or non-functional.

It will be appreciated that the terms "proximal" and "distal" may be used throughout the specification with reference to a direction of flow through either a catheter or a capillary. As used herein, the term "proximal" refers to the portion of the instrument through which the AO flows first, and the term "distal" refers to the portion of the instrument through which the AO subsequently flows. It will be further appreciated that for conciseness and clarity, spatial or directional terms such as "vertical," "horizontal," "up," "down," "clockwise," and "counterclockwise" may be used herein with respect to the illustrated embodiments. However, medical instruments may be used in many orientations and positions, and these terms are not intended to be limiting and absolute.

Joinder references (e.g., affixed, attached, coupled, connected, and the like) are to be construed broadly and may include intermediate members between a connection of elements and relative movement between elements. As such, joinder references do not necessarily infer that two elements are directly connected and in fixed relation to each other. As used herein, joinder references may also include two components that are molded as a single or unitary piece. Changes in detail or structure may be made without departing from the spirit of the invention as defined in the appended claims.

What is claimed is:

1. A catheter for infusing a carrier fluid supersaturated with a gas into a host liquid, the catheter comprising the following:
    a catheter tube defining a catheter tube longitudinal axis and comprising a catheter tube sidewall, a catheter tube proximal end adapted to receive the carrier fluid, and a catheter tube distal end, wherein an inner surface of said catheter tube sidewall defines a catheter lumen adapted to transport the carrier fluid; and
    a capillary comprising a capillary proximal end and a capillary distal end, wherein an inner surface of said capillary defines a capillary-lumen having a luminal surface free of crevices, and wherein said capillary is mounted to said catheter tube with said capillary proximal end located within said catheter lumen between said catheter tube proximal end and said catheter tube distal end, and said capillary lumen extending from said catheter lumen to outside said catheter tube, wherein said capillary lumen is adapted to transport said carrier fluid from said catheter lumen to outside of said catheter tube.

2. The catheter of claim 1, wherein said capillary further comprises a longitudinal axis arranged substantially parallel to said catheter tube longitudinal axis at a location where said capillary exits from said catheter tube.

3. The catheter of claim 1, wherein said capillary-comprises a longitudinal axis at said capillary distal end that forms a carrier fluid delivery angle relative to said catheter longitudinal axis, and wherein said carrier fluid delivery angle is an acute angle relative to a flow direction of the host liquid.

4. The catheter of claim 1, wherein said capillary distal end is mounted through said catheter tube sidewall, and wherein said catheter tube distal end is closed.

5. The catheter of claim 1, wherein said capillary distal end is potted into said catheter tube distal end such that said catheter tube distal end is closed except for an opening defined by said capillary lumen at said capillary distal end.

6. The catheter of claim 1, wherein said capillary comprises a plurality of capillaries, each capillary having a capillary distal end, and wherein said capillary distal ends are potted adjacent one another in said catheter tube distal end.

7. The catheter of claim 1 further comprising a second capillary having a second capillary proximal end, a second capillary distal end, and a second capillary lumen wherein said capillary distal end and said second capillary distal end are mounted through said catheter tube sidewall such that carrier fluid can exit from said capillary distal end and said second capillary distal end at a shallow angle relative to said catheter tube longitudinal axis.

8. The catheter of claim 1, wherein a distal portion of said catheter tube is folded back upon itself, thereby defining a distally-facing curve in said catheter tube.

9. The catheter of claim 8, wherein said distal portion of said catheter tube forms a pigtail configuration.

10. The catheter of claim 1, wherein said catheter tube distal end comprises a bend, and wherein said capillary is potted through said catheter sidewall along said bend such that an acute delivery angle relative to a flow direction of the host liquid is defined between said catheter tube longitudinal axis and a longitudinal axis of said capillary.

11. The catheter of claim 10, wherein said delivery angle is between 0-60 degrees.

12. A catheter for infusing a carrier fluid supersaturated with a gas into a flowing host liquid, the catheter comprising the following:
a catheter tube defining a catheter tube longitudinal axis and comprising a catheter tube sidewall, a catheter tube proximal end adapted to receive the carrier fluid, and a catheter tube distal end adapted for insertion into the host liquid, wherein an inner surface of said catheter tube sidewall defines a catheter lumen adapted to transport the carrier fluid;
a capillary comprising a capillary longitudinal axis, a capillary proximal end, and a capillary distal end; wherein said capillary defines an inner luminal surface free of crevices and adapted to transport the carrier fluid from the catheter lumen; and wherein said capillary is mounted with said capillary proximal end in said catheter lumen, said capillary proximal end located between said catheter tube proximal end and said catheter tube distal end, and said capillary distal end mounted through said catheter tube sidewall.

13. The catheter of claim 12, wherein said capillary proximal end floats freely in said catheter lumen, and wherein said capillary distal end is mounted in a channel through said catheter tube sidewall such that fluid may exit said capillary in substantial alignment with a direction of flow of the host liquid.

14. The catheter of claim 13, wherein said capillary distal end defines an end surface transverse to said capillary longitudinal axis.

15. The catheter of claim 13, wherein said capillary distal end defines an end surface oblique to said capillary longitudinal axis and flush with an outer surface of said catheter tube sidewall.

16. The catheter of claim 12, wherein said capillary is mounted through said catheter tube sidewall such that fluid exits said capillary at an acute delivery angle relative to a flow direction of the host liquid.

17. The catheter of claim 12, wherein said catheter is adapted to deliver the carrier fluid at a flow rate of about 8 mL/min. to about 160 mL/min.

18. The catheter of claim 12, wherein said capillary has an inner diameter of between about 50 microns and about 100 microns.

19. The catheter of claim 12, wherein said capillary has an inner diameter of 50 microns and a length of 1-4 cm.

20. The catheter of claim 12, wherein said capillary is constructed from plastic resin.

21. The catheter of claim 12, wherein said capillary is constructed from thermoplastic polymer.

22. The catheter of claim 12, wherein said capillary is constructed from metal.

23. The catheter of claim 22, wherein said capillary is constructed from Nitinol.

24. The catheter of claim 12, wherein said capillary constructed from silica.

25. The catheter of claim 24, wherein said capillary is constructed from fused silica and has an inner diameter of 100 microns and is 2-8 inches long.

26. The catheter of claim 12, wherein said catheter tube comprises a plurality of bends creating a plurality of obstruction-free zones, and wherein said capillary is mounted in said catheter tube sidewall so as to deliver said carrier fluid exiting said capillary during use of the catheter into one of said plurality of obstruction-free zones at an acute delivery angle measured between said capillary longitudinal axis and said catheter tube longitudinal axis relative to a flow direction of the host liquid.

27. The catheter of claim 12, wherein said catheter tube comprises a plurality of bends, and wherein said capillary is mounted in a hole through said catheter tube sidewall such that carrier fluid may exit said capillary at a shallow angle relative to said catheter tube longitudinal axis.

28. The catheter of claim 27, wherein said catheter tube defines a sigmoid curve.

29. The catheter of claim 27, wherein said catheter tube defines a sinusoidal curve.

30. The catheter of claim 27, wherein said catheter tube defines a helical structure.

31. The catheter of claim 30, wherein said catheter tube has an outer diameter of approximately 5 French, and wherein said helical structure has an outer diameter of approximately 1 cm.

32. The catheter of claim 30, wherein through said catheter tube sidewall defines a hole longitudinal axis, wherein said hole longitudinal axis is arranged radially about said catheter tube longitudinal axis so as to point toward a geometric center of said helical structure at an angle of approximately 20-30 degrees relative to a flow direction of the host liquid.

33. The catheter of claim 30, wherein said distal end of said capillary is mounted in said catheter tube sidewall along an inner aspect of said helical structure approximately 1-2 cm apart axially.

34. The catheter of claim 27, wherein said catheter tube defines a substantially two-dimensional configuration comprising said plurality of bends and creating a plurality of fluid-delivery regions.

35. The catheter of claim 27, wherein said catheter tube defines a substantial three-dimensional configuration, creating a fluid-delivery volume.

36. The catheter of claim 12, wherein said capillary is mounted in said catheter tube sidewall so as to minimize interaction between the carrier fluid exiting said capillary and the catheter tube.

37. The catheter of claim 12, wherein each said capillary distal end is mounted through said catheter sidewall at a pass-through location, and wherein each pass-through location is separated from a next adjacent pass-through location by at least 3 mm.

38. The catheter of claim 12, wherein each said capillary distal end is mounted in said catheter tube sidewall and separated from a next adjacent capillary distal end by between 5 mm and 3 cm.

* * * * *